United States Patent [19]

Rao

[11] Patent Number: 4,619,943

[45] Date of Patent: Oct. 28, 1986

[54] **NEOLIGNANS OF *SAURURUS CERNUUS* L AND ANALOGUES THEREOF**

[76] Inventor: Koppaka V. Rao, 3750 NW. 16th Pl., Gainesville, Fla. 32605

[21] Appl. No.: 648,920

[22] Filed: Sep. 10, 1984

Related U.S. Application Data

[63] Continuation-in-part of Ser. No. 270,358, Jun. 4, 1981, abandoned.

[51] Int. Cl.$^4$ .................... A61K 31/36; A61K 31/34; C07D 317/44; C07D 307/02
[52] U.S. Cl. ................................. 514/464; 514/461; 514/471; 549/435; 549/499; 549/500; 549/501; 549/502
[58] Field of Search ...................... 549/435, 500, 502; 514/461, 464, 471

[56] References Cited

U.S. PATENT DOCUMENTS 4,539,332 9/1985 Biftu et al. ..................... 514/461

FOREIGN PATENT DOCUMENTS 50-121262 9/1975 Japan .................................. 549/502
54-106460 8/1979 Japan .................................. 549/502

OTHER PUBLICATIONS

F. M. Alvarez, "Neolignans of *Saururus cernuus* L", Ph.D. Dissertation, University of Florida, Gainesville, Florida, Jun. 1981 (available to the public Jul., 1981).
K. V. Rao et al., "Manassantins A/B and Saucerneol: Novel Biologically Active Lignoids from *Saururus cernuus*", Tet. Lett., 24, 4947 (1983).
K. V. Rao et al., "Chemistry of *Saururus cernuus*, I. Saucernetin, A New Neolignan", J. Nat. Prods., 45, 393 (1982).
A. Hernandez et al., "Neo-Olivil, A New Lignan from *Thymus longiflorus*", Phytochem., 20, 181 (1981).
L. V. Tutupalli et al., "Saururaceae. V. Composition of Essential Oil from Foliage of *Houttuynia cordata* and Chemosystematics of Saururaceae", Lloydia, 38, 92 (1975).
L. V. Tutupalli, "Phytochemistry of Saururaceae Essential Oils", Ph.D. Dissertation, University of the Pacific, Stockton, California (1974), pp. iv, v, and 1-14.
J. L. Hartwell, "Plants Used Against Cancer, A Survey", Lloydia, 34, 204 (1971).
D. L. Phares, "*Saururus cernuus*", Am. J. Pharm., 39, 468 (1867).
O. R. Gottleib, "Neolignans", Progress in the Chemistry of Organic Natural Products, W. Herz et al., Eds., Springer Verlag, New York, 35, 1 (1978).
A. J. Birch et al., "Some Stereochemical Studies of Lignans", J. Chem. Soc., 4471 (1958).
F. E. King et al., "The Chemistry of Extractives from Hardwoods, Part XXXVI, The Lignans of *Guaiacum officinale* L.", J. Chem. Soc., 4011 (1964).
J. G. Blears et al., "The Constituents of Natural Phenolic Resins, Part XXIV, A Synthesis of Galgravin.", J. Chem. Soc., 1985 (1958).
N. S. Crossley et al., "Naturally Occurring Oxygen Heterocyclics, Part XI, Veraguensin.", J. Chem. Soc., 1459 (1962).
K. V. Sarkanen et al., "Oxidative Dimerizations of (E)- and (Z)-Isoeugenol (2-methoxy-4-propenylphenol) and (E)- and (Z)-2,6-Dimethoxy-4-propenylphenol.", J. Chem. Soc., Perkin I, 1869 (1973).
S. T. Murphy et al., "Some Constituents of *Austrobaileya scandens* (Austrobaileyaceae): Structures of Seven New Lignans.", Aust. J. Chem., 28, 81 (1975).
N. V. Riggs et al., "Some Constituents of *Piptocalyx moorei* Oliv.", Aust. J. Chem., 15, 305 (1962).
P. L. Majumder et al., "Lignans from *Machilus edulis*, Phytochem., 11, 811 (1972).
K. V. Rao et al., "Manassantins A/B: Novel Neuroleptic Neolignans", Abstract 122, The Abstracts of the 9th International Congress of Pharmacology, London, Jul., 1984, MacMillan Press.

*Primary Examiner*—Ethel G. Love
*Attorney, Agent, or Firm*—Robert M. Kennedy; H. Robinson Ertelt

[57] ABSTRACT

Novel phenylpropanoid neolignans isolated from *Saururus cernuus* L and synthetic or semi-synthetic analogs thereof having neuroleptic, insecticidal, or nematicidal activity are disclosed.

26 Claims, 9 Drawing Figures

NEOLIGNANS OF *SAURURUS CERNUUS* L AND ANALOGUES THEREOF

BACKGROUND OF THE INVENTION

This application is a continuation-in-part of U.S. application Ser. No. 270,358, filed June 4, 1981, now abandoned, incorporated herein by reference.

This invention relates to a group of novel substances which are useful in producing central nervous system depressant effects in warm blooded animals, specifically of the type of neuroleptic activity, to processes for their isolation, purification and synthesis and to the synthesis of analogues and derivatives thereof. The novel compounds also have insecticidal and nematicidal properties. More particularly, the invention relates to the isolation from *Saururus cernuus* L (N.O. Saururaceae) of novel compounds designated herein as SC-5, SC-6, SC-7, SC-8, SC-9 and others which show characteristic effects of neuroleptic drugs (also known as major tranquilizers or antipsychotic agents) in experimental animals as evidenced by sedation, tranquilization, inhibition of amphetamine-induced agitation, hyperactivity, stereotypy, body hydration and other characteristic effects. Compounds with said type of activity are generally useful for the treatment of various forms of psychoses, schizophrenia and for counteracting effects of central stimulants, psychedelic drugs and narcotic withdrawal. The structures of SC-5, SC-6, SC-7, SC-8 and SC-9 are different from any of the known neuroleptic agents either isolated from plants or synthesized.

SUMMARY AND SCOPE OF THE INVENTION

The title compounds SC-5, SC-6, SC-7, SC-8 and SC-9 are constituents of the plant *Saururus cernuus* L (N.O. Saururaceae), a native of North America and commonly known as lizard's tail. These compounds are colorless, neutral, lipophilic substances which belong to the broad class of neolignans and are collectively referred to herein as the "SC-neolignans". They may be isolated from the whole plant by extraction with a suitable organic solvent, concentration of the extract and processing of the concentrate by a series of chromatographic separation steps. By such a procedure, at least ten compounds, SC-1 through SC-10, may be isolated from the extract of the whole plant. There is evidence for the presence of several other minor constituents whose characteristics are not yet fully known, although they bear general similarity to the SC-neolignans. All of the ten compounds isolated so far belong to the broad class of neolignans. Compound SC-8, the major active compound, shows useful neuroleptic, insecticidal, and nematicidal activity, and SC-5, SC-6, SC-7 and SC-9 generally resemble SC-8 in physical and chemical characteristics and biological activity. SC-8 shows significant activity in potentiating sedatives of the pentobarbital type, and in inhibiting the hyperactivity, agitation, and other effects induced by central nervous system stimulants of the amphetamine class. The structure and stereochemistry of each of SC-6, SC-7 and SC-8 establish that they are different from the neolignans previously described in the literature. The present novel compounds are also of a different structural type than any of the known synthetic drugs having neuroleptic activity.

The present invention is not limited to the above mentioned specific compounds, but also includes the total extract of the plant made by using various solvents, fractions prepared from these extracts that may contain one or more of these components and other minor components that have not yet been obtained in a homogeneous form but nevertheless show neuroleptic activity. The invention not only includes the novel compounds themselves, but also insecticidal and nematicidal compositions of them, their pharmaceutical dosage forms containing a variety of nontoxic diluents suitable for oral or parenteral administration, and derivatives prepared to enhance the ease of administration, duration of action, degree of effectiveness, or the reduction of toxic side effects. The invention includes the natural compounds and totally or partially synthesized compounds having the same general chemical structure as the natural materials, as well as biologically active analogues, congeners, and portions of the structures which represent the essential active moiety of the drugs. Various combinations containing 10–90% of these compounds and the rest comprised of other natural or synthetic neuroleptic, insecticidal, or nematicidal agents, are also included in this invention. The present novel compounds are useful in medical and scientific research as new models of neuroleptic drugs and in animal studies to counteract the effects of central stimulants, narcotics and other psychoactive drugs, in addition to being useful as insecticides or nematicides or as models after which insecticides or nematicides may be designed.

These active substances are isolated from the plant known as *Saururus cernuus* L (N.O. Saururaceae). A description of the plant taken from "The Wild Flowers of New York" by Homer D. House, The University of the State of New York, Albany, N.Y. 1923, is given below:

"Stem 2 to 5 feet high from a slender root stock, jointed, pubescent when young, becoming smooth. Leaves ovate, thin, palmately five to nine ribbed, dark green, entire, deeply cordate at the base, acuminate, 3 to 6 inches long, 2 to 3½ inches wide; petioles sheathing the stem at the enlarged nodes; the stem terminating in one or two elongated white spikes, their tips drooping in flower. Flowers fragrant, small, white, without any perianth; stamens six to eight, white, spreading; ovary consisting of three or four carpels united at the base, becoming slightly fleshy and strongly wrinkled in fruit. In swamps and shallow water, Rhode Island to Florida, west to Southern Ontario, Minnesota and Texas. Flowering from June to August."

A voucher sample of the plant is placed in the herbarium of the University of Florida. In spite of this, the invention is not limited to the isolation of the above mentioned active compounds from this particular plant whether naturally grown, hybridized, or grown in cell culture, but includes any other plant related or otherwise from which these compounds may be isolated. In the case of *Saururus cernuus* L, the whole plant is used either fresh or air-dried after an initial step of size-reduction.

The prior art on this plant, *Saururus cernuus* L, is generally confined to a study of the volatile oil constituents and the isolation of a number of terpenoid compounds for which no specific biological activity has been ascribed. The compounds described herein, the SC-neolignans, are structurally different from these terpenoid compounds, have not been previously isolated in biologically or chemically pure form, and possess valuable properties which make them useful in both pharmaceutical and agricultural applications.

DETAILED DESCRIPTION OF THE INVENTION

Figure 1:
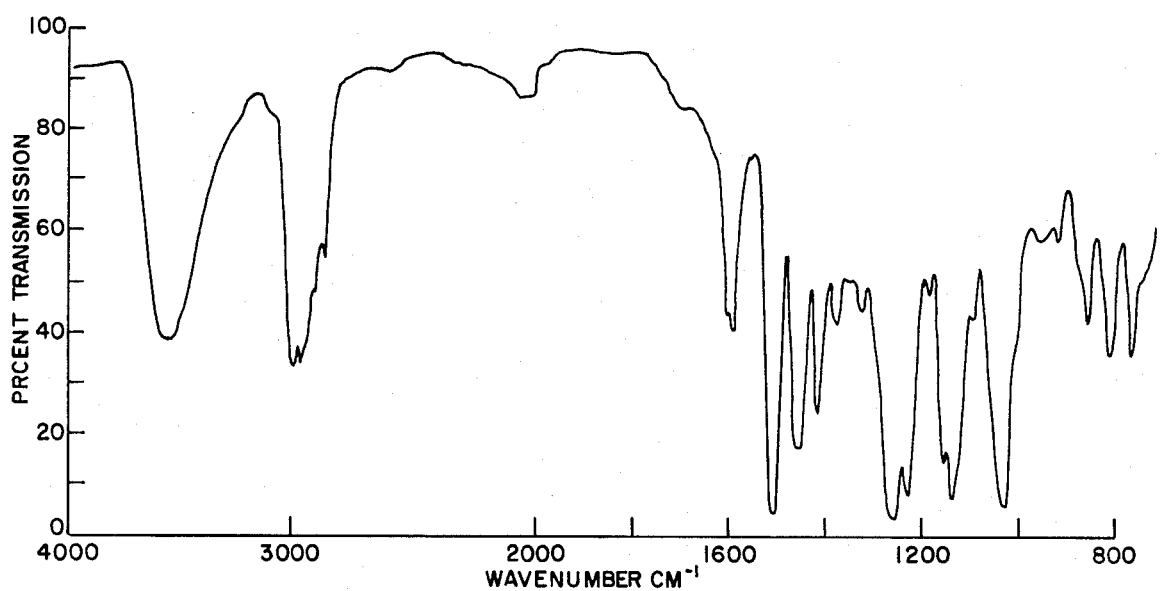

For the extraction of the present active compounds, a variety of solvents may be used either singly or in combination with each other. Suitable solvents include, for example, hydrocarbons, alcohols, ethers, halohydrocarbons, ketones, esters, water and mixtures thereof. Hydrocarbon solvents include aromatic hydrocarbons such as benzene, toluene, and the xylenes, as well as aliphatic and cycloaliphatic hydrocarbons, preferably of 5 to 8 carbon atoms, such as pentane, hexane, heptane, and octane, isomers thereof, and the corresponding cyclic materials, for example, cyclohexane. Ether solvents include aliphatic ethers such as diethyl ether and cyclic ethers such as tetrahydrofuran. Halohydrocarbon solvents may be haloalkanes such as methylene chloride or halophenyl compounds such as chlorobenzene. Ketone solvents will usually be aliphatic ketones of 3 to 6 carbon atoms, for example, acetone or ethyl methyl ketone, or a cycloaliphatic ketone such as cyclopentanone or cyclohexanone. Aliphatic ester solvents such as ethyl or methyl acetate and alcohol solvents, frequently of 1 to 4 carbon atoms, are also useful. Extraction may be by batch or continuous process or vapor-phase method at ambient or elevated temperatures.

In a preferred extraction method using 95% ethanol, three extractions at room temperature by batch percolation were carried out, each extraction lasting for two days. The combined extracts were concentrated by using heat, preferably under reduced pressure, to a thick syrup. The viscous concentrate was partitioned between water in the pH range of 2.0–10.0 and a water-immiscible solvent, preferably, ethyl acetate, chloroform, benzene, or ether, whereby the active materials (the SC-neolignans) passed into the organic layer. The extraction and partitioning process provides a solution of SC-neolignans substantially free of extraneous plant materials such as water-soluble materials and materials that are insoluble in the water-immiscible partitioning solvent. The water-immiscible solvent layer was concentrated and processed by chromatography to obtain a crude mixture of the active components before final chromatography. In the column chromatography procedure, the concentrate from the partitioning above was taken up in a suitable solvent such as benzene and added to a column made up of silica gel. Other solvents and solvent combinations including hexane, chloroform, toluene, and the like may be used, and adsorbents such as alumina or a magnesium silicate such as Florisil ® (a complex magnesium silicate available through Floridin Co., Berkeley Springs, WV 25411) are also suitable. Gross separation into three groups of different polarity was achieved by elution with solvents of increasing polarity, preferably by using benzene, 5–25% acetone in benzene, and 1–10% methanol in benzene. The neuroleptic activity is generally found in the fraction of intermediate polarity after concentration to dryness. Alternatively, a series of partitions between different pairs of solvents may be carried out to achieve a gross separation into fractions of varying polarity.

For further purification and separation of the active compounds, adsorption chromatography, preferably using silica gel, was employed in which the mixture was added as a solution in benzene in a proportion of 15–35 g of adsorbent per gram of mixture in a column of suitable size. Other adsorbents commonly used in chromatography including alumina (acidic, neutral or basic), magnesium silicate such as Florisil, partially etherified cross-linked dextran such as Sephadex ® (Pharmacia Fine Chemicals, Piscataway, NJ 08854), and polyamide are also satisfactory. The column was eluted with benzene, followed by increasing concentrations of acetone (0–25%) in benzene which can be made in discrete steps or in a gradient fashion. Fractions of suitable volume were collected, tested by uv adsorption intensity at 280 nm and thin-layer chromatography (silica gel plates, 5–25% acetone/benzene, visualization: uv light or spray with 1% sulfuric acid and heat to generate crimson red spots), combined based on their composition, and concentrated to dryness. Alternatively, partition chromatography using Sephadex LH20 as the support with 50–80% methanol in water as the stationary phase and ligroin with a 0–75% benzene gradient as the mobile phase may be used to effect this further separation into groups based on polarity.

For final purification, high performance liquid chromatography may be used for obtaining biologically pure individual components. A variety of commercially available column packings, with eluting solvents such as aliphatic/aromatic hydrocarbons, halohydrocarbons, lower alcohols, or lower aliphatic ketones may be employed at pressures ranging from 0–5000 p.s.i. for an efficient separation of the individual components in chemical and biological purity. The individual components were redissolved in minimum volumes of benzene, filtered, diluted with three volumes of hexane and filtered. Using such a procedure, SC-1, SC-2, SC-3, SC-4, SC-5, SC-6, SC-7, SC-8, SC-9 and SC-10 were isolated. Of these, SC-5, SC-7, SC-8 and SC-9 were found to be neuroleptically active with SC-8 being the major active principle. SC-6 is useful for the synthesis of SC-7, SC-8, and a variety of analogues.

Figure 5:
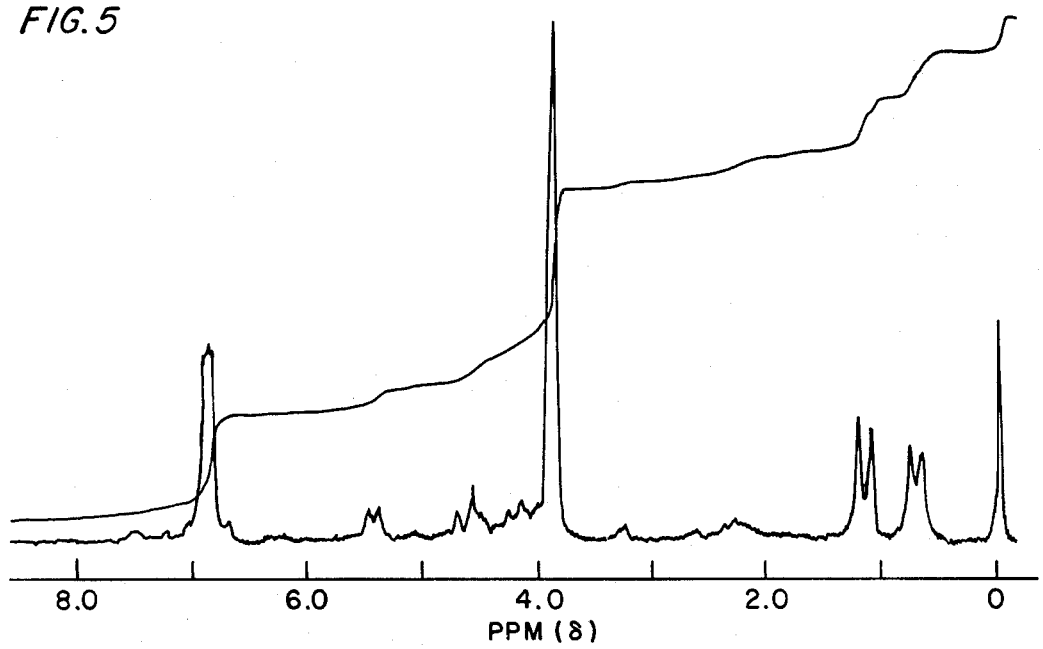

SC-8, as prepared by the procedure described above, is a colorless amorphous solid with an apparent melting point of 80°–85°. It behaved as a homogeneous compound in thin-layer chromatography (silica gel plates, 15% acetone/benzene, Rf 0.3; 10% methanol/-chloroform, Rf 0.65) and high performance liquid chromatography (Partisil ® 5/25 column, 1% methanol/-chloroform as eluent at 1.5–2.5 ml/min, retention time: 5.8 minutes). Partisil is a brand of silica gel sold by Whatman, Inc., Clifton, N.J. Other brands of silica gel may also be used. SC-8 was optically active, $[\alpha]_D - 100$ (C=1, chloroform) and was readily soluble in alcohols, acetone, chloroform, benzene and ethyl acetate, but sparingly in ether, and very slightly in hexane or water. Elemental analysis of SC-8 gave: C, 68.66; H, 7.30; calculated for $C_{42}H_{52}O_{11}$ C, 68.83; H, 7.15. SC-8 showed a characteristic ultraviolet absorption spectrum with maxima at 212, 235 and 280 nm and log ε values of 4.82, 4.62 and 4.16 respectively. The infrared spectrum (KBr pellet, FIG. 1) showed the following bands: 3500, 2995, 2960, 1610, 1590, 1510, 1460, 1420, 1380, 1330, 1265, 1230, 1190, 1160, 1140, 1100, 1030, 960, 920, 860, 810, 765 cm$^{-1}$; and the $^1$H nmr spectrum (CDCl$_3$, FIG. 5), the following signals: τ2.95–3.30, m, 12H; τ4.50, 4.60, d, J=6 Hz, 2H; τ5.30, 5.43, d, J=8 Hz, 2H; τ5.90, m, 2H; τ6.14, s, 18H; τ7.70, m, 2H; τ8.80, 8.90, d, J=6 Hz, 6H; τ9.22, 9.33, d, J=6 Hz, 6H. The $^{13}$C nmr spectrum of SC-8 showed the following signals (ppm): 14.7, 16.8, 44.0, 55.7, 78.1, 83.2, 83.6, 110.1, 110.8, 118.4, 118.6, 119.8, 132.6, 136.2, 146.3, 148.7, 148.9 and 150.4.

These spectral data suggested that SC-8 belonged to the group of natural products known as neolignans (Gottleib, O. R., Progress in the Chemistry of Natural Products, Herz, W., Griesel-bach, H. and Kirby, G. W. Eds., Springer Verlag, New York 35, 1 (1978)). Neolignans are compounds derived from two units of allylbenzene or two units of propenylbenzene or one unit of each and are widely distributed among natural products.

Acetylation of SC-8 formed a diacetate, $C_{46}H_{56}O_{13}$; ir: 1735 cm$^{-1}$; nmr: $\tau$8.80,s, 6H, thus showing the presence in SC-8 of two hydroxyl groups. Lack of base-induced uv-spectral shifts showed that these were both alcoholic hydroxyls.

The following are some of the reactions of SC-8 which not only serve to characterize the compound but also permit one to assign structure 1 for the active compound.

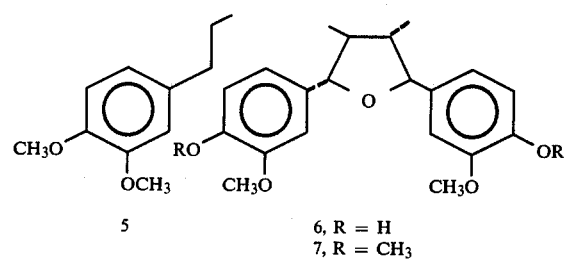

5

6, R = H
7, R = CH$_3$

When SC-8 was heated with p-toluenesulfonic acid in benzene or with other acids under a variety of conditions, two products were formed in the ratio of 2:1: the major compound being 3,4-dimethoxyphenylacetone 8 and the minor compound being a phenolic substance 9 which on methylation and dehydrogenation with Pd/C

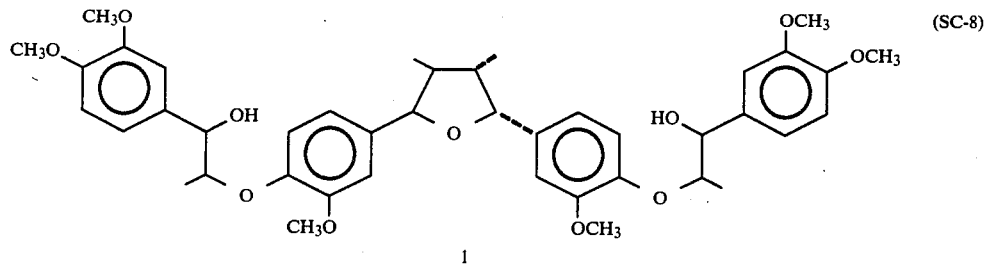

1 (SC-8)

gave the known 6,7-dimethoxy-4-(3,4-dimethoxy)phenyl-2,3-dimethylnaphthalene 10 (F. E. King and J. G. Wilson, J. Chem. Soc., 4011 (1964)).

Oxidation of SC-8 with alkaline potassium permanganate gave veratric acid 2, 3,4-dimethoxyphenylglyoxalic acid 3, and the acid 4 whose structure was confirmed by synthesis.

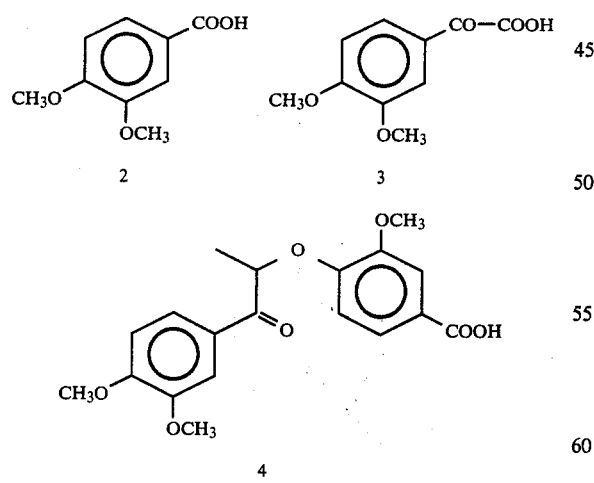

2

3

4

Hydrogenolysis of SC-8 with Pd/C gave 3,4-dimethoxyphenylpropane 5 and a phenolic product 6, $C_{20}H_{24}O_5$, which on methylation with dimethyl sulfate formed 7, identical with the known neolignan galbelgin (A. J. Birch, B. Milligan, E. Smith and R. N. Speake, J. Chem. Soc., 4471 (1958)).

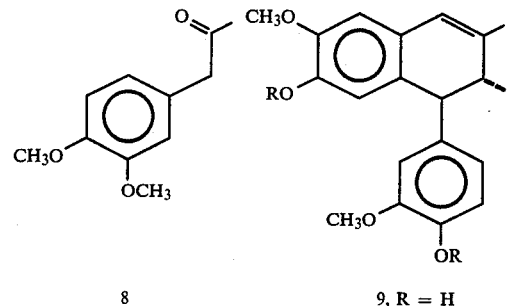

8

9, R = H
9a, R = CH$_3$

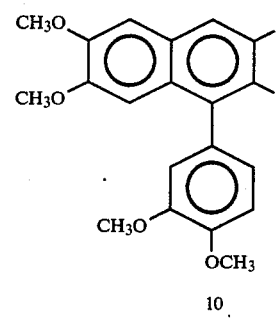

10

Oxidation of SC-8 with dichlorodicyanoquinone gave a product, 11, having a characteristic uv-spectrum of a 2,5-diarylfuran. When 11 was heated with Pd/C followed by methylation, it formed 3,4-dimethoxyphenylpropane 5 and 2,5-bis(3,4-dimethoxy)phenyl-3,4-dimethylfuran 12 (F. E. King and Wilson, vide supra).

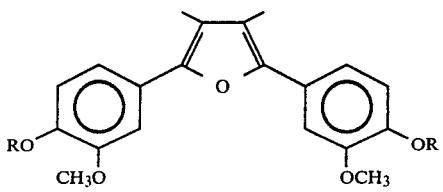

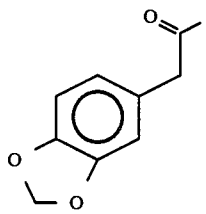

13

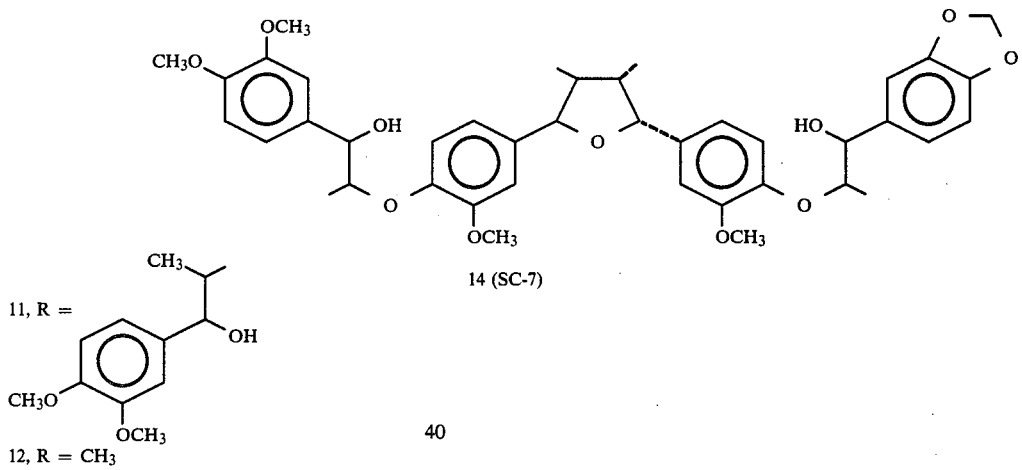

14 (SC-7)

11, R = [structure with CH₃, CH₃O, OCH₃, OH]

12, R = CH₃

Structure 1 assigned for SC-8 is a novel neolignan representation consisting of four phenylpropanoid units, instead of two as is normally found in neolignans. For this reason, it must be considered as the first member of a group of dineolignans. SC-8 has the chemical name 2α,5β-bis[3-methoxy-4-{threo-3-hydroxy-3-(3,4-dimethoxyphenyl)}isopropoxyphenyl]-3α,4β-dimethyltetrahydrofuran.

Figure 2:
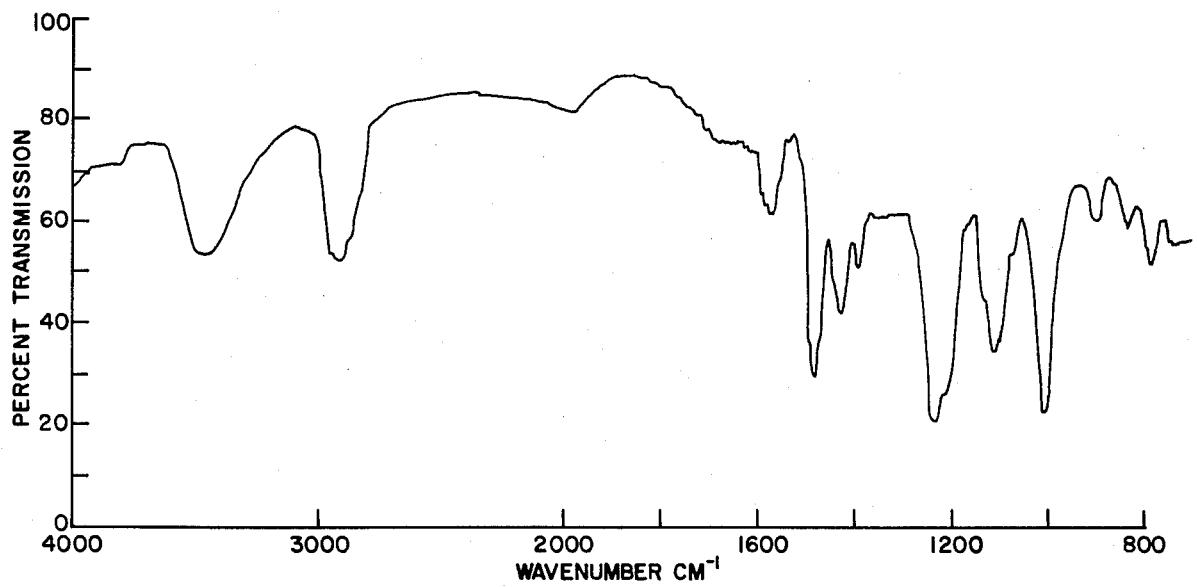
Figure 6:
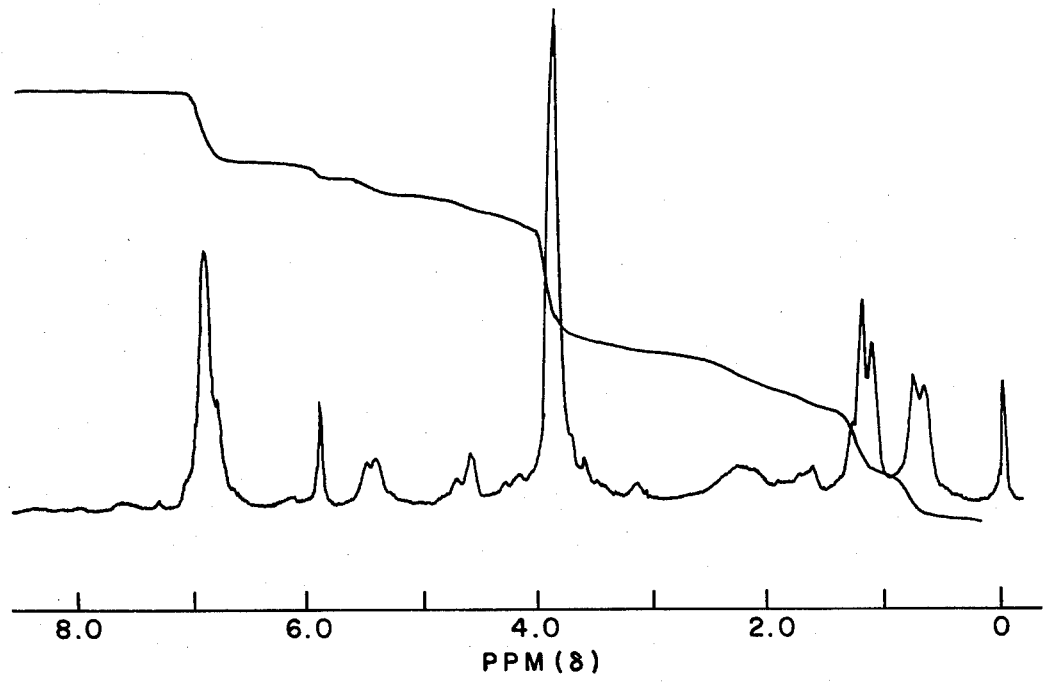

SC-7, $C_{41}H_{48}O_{11}$, $[\alpha]_D$-99 (C =1, chloroform) is a colorless amorphous solid with uv and ir spectral properties very similar to those of SC-8. The compound had an Rf value of 0.36 on silica gel thin-layer chromatographic plates when eluted with 15% acetone in benzene. The high performance liquid chromatographic retention time was 5.1 minutes on a Partisil P x S 5/25 column with 1% methanol in chloroform as eluent. The infrared spectrum (KBr pellet, FIG. 2) showed the following bands: 3460, 2950, 2900, 1610, 1590, 1505, 1450, 1415, 1255, 1230, 1140, 1030, 920, 855, 805, and 760 cm¹. The nmr spectrum (CDCl₃, FIG. 6): τ2.90–3.33 m, 12H; τ4.12, s, 2H; τ4.52, 4.62, d, 2H; τ5.30, 5.43, d, 2H; τ5.83, m, 2H; τ6.10, s, 12H; τ7.73, m, 2H; τ8.80, 8.90, d, 6H; τ9.23, 9.33, d, 6H was very similar to that of SC-8 except that it showed the presence of a methylenedioxy group and two less methoxyls. Acetylation gave a diacetate, $C_{45}H_{52}O_{13}$; ir: 1735 cm⁻¹; (Ac O Alk) nmr: τ8.80, s, 6H. Acid hydrolysis formed three products in an equimolar ratio: 3,4-dimethoxyphenylacetone 8, 3,4-methylenedioxyphenylacetone 13 and the phenolic product 9 referred to above. Structure 14 was assigned to SC-7 which was very similar to that of SC-8 except that a 3,4-dimethoxyphenyl unit was replaced by a 3,4-methylenedioxyphenyl unit. The chemical name for SC-7 is 2α-[3-methoxy-4-{threo-3-hydroxy-3-(3,4-dimethoxyphenyl)}isopropoxyphenyl]-5β-[3-methoxy-4-{threo-3-hydroxy-3-(3,4-methylenedioxyphenyl)}isopropoxyphenyl]-3α,4β-dimethyltetrahydrofuran.

Figure 3:
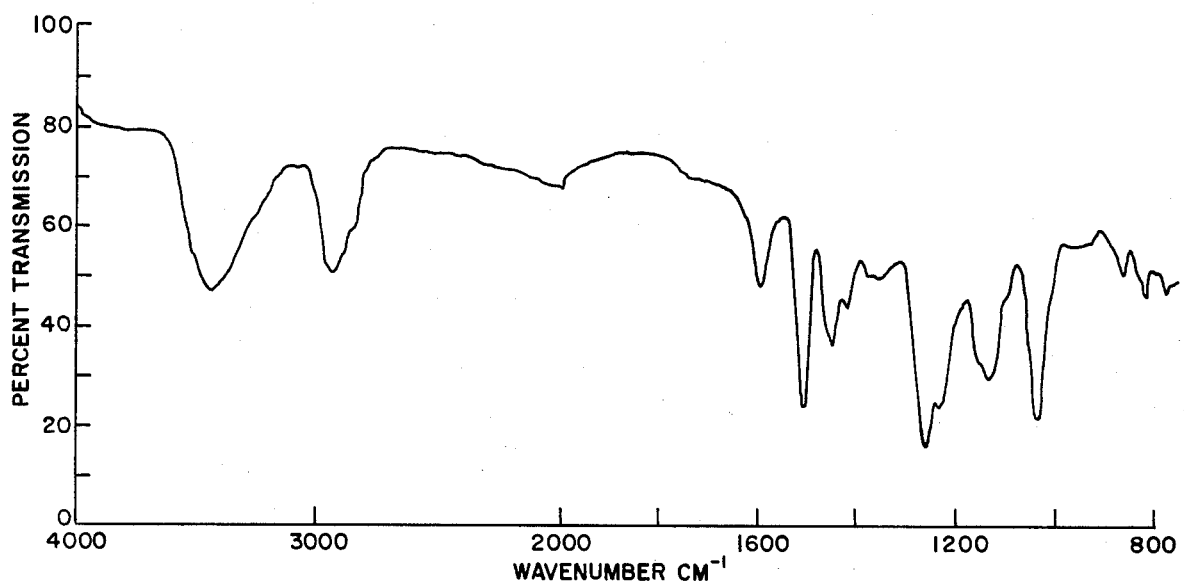
Figure 7:
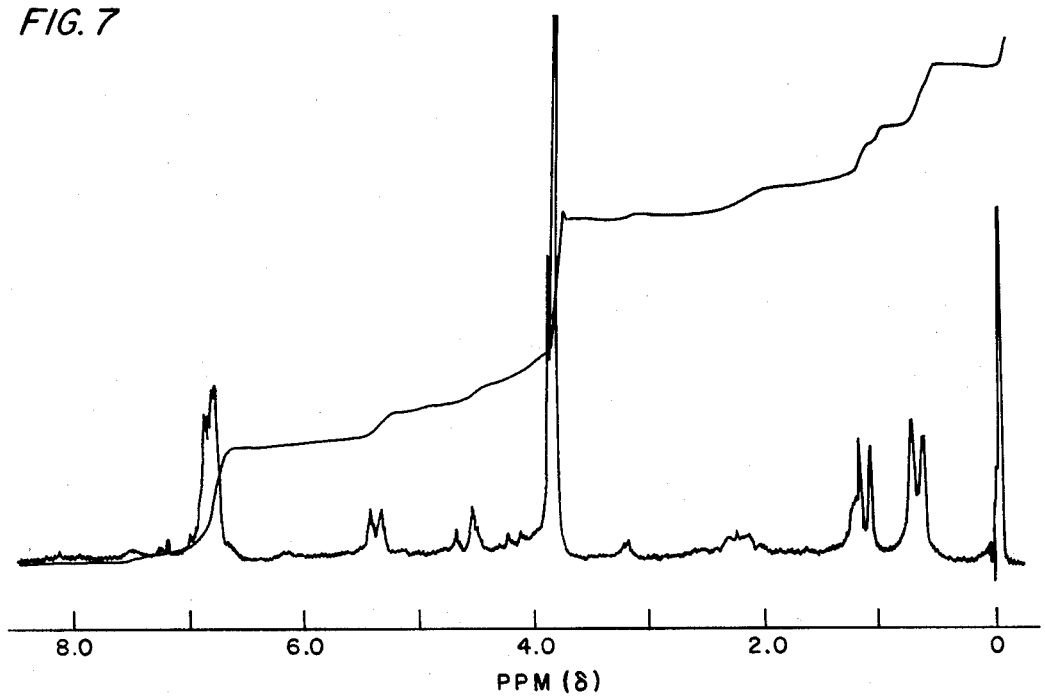

SC-6, $C_{31}H_{38}O_8$, colorless solid, $[\alpha]_D$-52.3 (C =1 chloroform) also showed uv and ir spectral data very similar to those of SC-8, except for signals showing the presence of a phenolic group. SC-6 had an Rf value of 0.38 on silica gel thin-layer chromatography plates when eluted with 15% acetone in benzene. The infrared spectrum (KBr pellet, FIG. 3) showed bands at 3460, 2960, 1600, 1510, 1453, 1420, 1365, 1260, 1230, 1158, 1138, 1030, 950, 920, 850, 810, and 765 cm⁻¹. Its nmr spectrum (CDCl₃, FIG. 7): τ3.00–3.27, m, 9H; τ4.52, 4.62, d, 2H; τ5.29, 5.42, d, 1H; τ5.84, m, 1H; τ6.10, s, 12H; τ7.74, m, 2H; τ8.79, 8.89, d, 3H; τ9.25, 9.35, d, 6H, while basically similar to that of SC-8, showed the absence of one phenylpropanoid unit. Acetylation of SC-6 gave a diacetate, $C_{35}H_{42}O_{10}$, ir: 1735, 1760 cm⁻¹ and nmr; τ7.70, s, 3H; τ8.00, s, 3H with evidence for one alcoholic and one phenolic hydroxyl. Acid hydrolysis of SC-6 led to an equimolar mixture of 8 and 9. These led to the assignment of structure 15 for SC-6. This structure was confirmed by the reaction of SC-6 with 2'-bromo-3,4-dimethoxypropiophenone and potassium carbonate to give a product 16 which on reduction with sodium borohydride gave 17 which was identical with SC-8 except for a slight stereochemical difference.

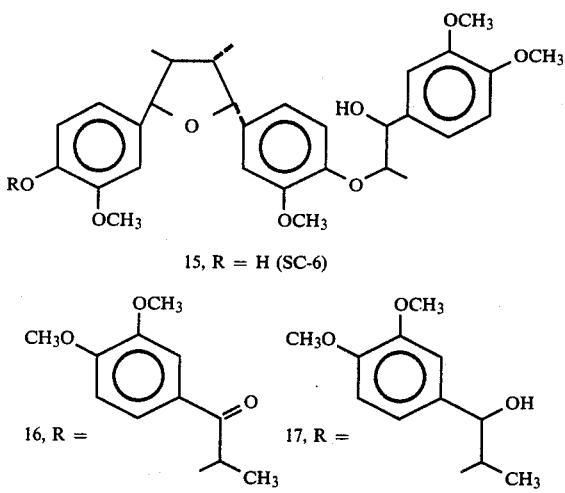

15, R = H (SC-6)

16, R = (structure with CH3O, OCH3, C=O, CH-CH3)

17, R = (structure with CH3O, OCH3, CH(OH)-CH-CH3)

The structures of SC-7 and SC-8 have three points where stereochemistry must be clarified: the central tetrahydrofuran system and the two phenylpropanoid chains. The tetrahydrofuran system has six possible orientations of which representatives of five are known so far. These are: galgravin 18 (A. J. Birch, B. Milligan, E. Smith and R. N. Speake, J. Chem. Soc., 4471 (1958)), tetrahydrofuroguaiacin 19 (J. E. Bleas and R. D. Haworth, J. Chem. Soc., 1985, (1958)), galbelgin 7 (vide supra), veraguensin 20 (N. S. Crossley and C. Djerassi, J. Chem. Soc., 1459 (1962)) and SC-2 21, the newest member isolated from *Saururus cernuus* L in the present work.

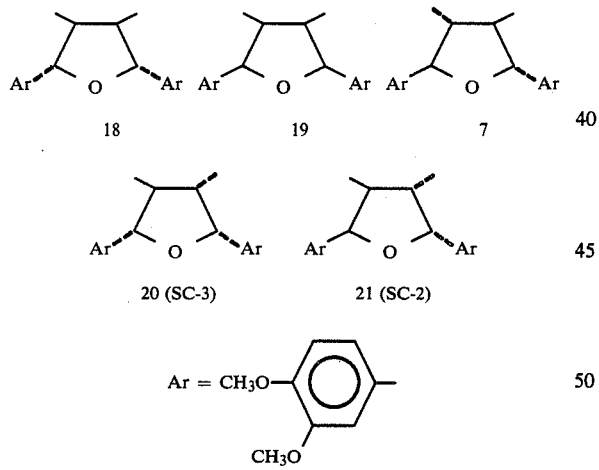

The nmr spectral signals of SC-8, SC-7 and SC-6 attributed to the tetrahydrofuran system corresponded closely with those of SC-2 (21) and differed from those of the other members, thus showing that SC-8 as well as SC-7 and SC-6 have the same stereochemistry as in SC-2. NMR analysis showed the relative stereochemistry to be cis/trans/cis as in SC-2. The chemical names and structures assigned herein for the present compounds are given to show the relative configuration of cis/trans/cis about the tetrahydrofuran ring, but are not intended to show the absolute configuration.

The phenylpropanoid units of SC-7 and SC-8 can exist as both threo, both erythro or threo/erythro. The nmr spectral signals corresponded closely with those of the threo isomers of known model compounds (K. V. Sarkanen and A. F. A. Wallis, J. Chem. Soc., Perkin I, 1869 (1973)), but not with the erythro isomers, thus indicating a threo/threo orientation for both these compounds. A similar argument assigns a threo configuration for the phenylpropanoid chain of SC-6. When SC-6 was converted to semisynthetic SC-8 (17), the product showed nmr spectrum characteristic of both threo and erythro forms. Reduction of model compounds related to 16 with sodium borohydride is known to give the erythro form exclusively (K. V. Sarkanen and A. F. A. Wallis, vide supra).

In addition to the compounds SC-2, SC-6, SC-7 and SC-8 described above, four known compounds were isolated from *Saururus cernuus* L: SC-1, the same as austrobailignan-5, 22, [S. T. Murphy, E. Ritchie and W. C. Taylor, Aust. J. Chem. 28, 81 (1975)]; SC-3, the same as veraguensin, 20, described above; SC-4, the same as calopiptin, 24, [N. V. Riggs and J. B. Stevens, Aust. J. Chem., 15, 305 (1962)]; and SC-10, the same as guaiacin, 23, [P. L. Majumder, A. Chatterjee, and G. C. Sengupta, Phytochem. 11, 814 (1972)].

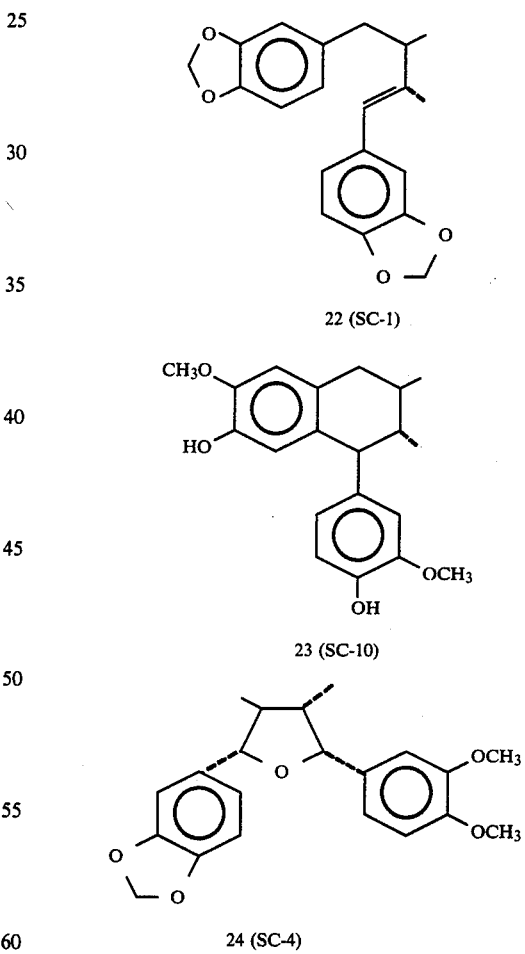

The structures of SC-5 and SC-9 have not yet been elucidated, but the spectral properties of them indicate a close similarity to the structures of the other members.

Figure 8:
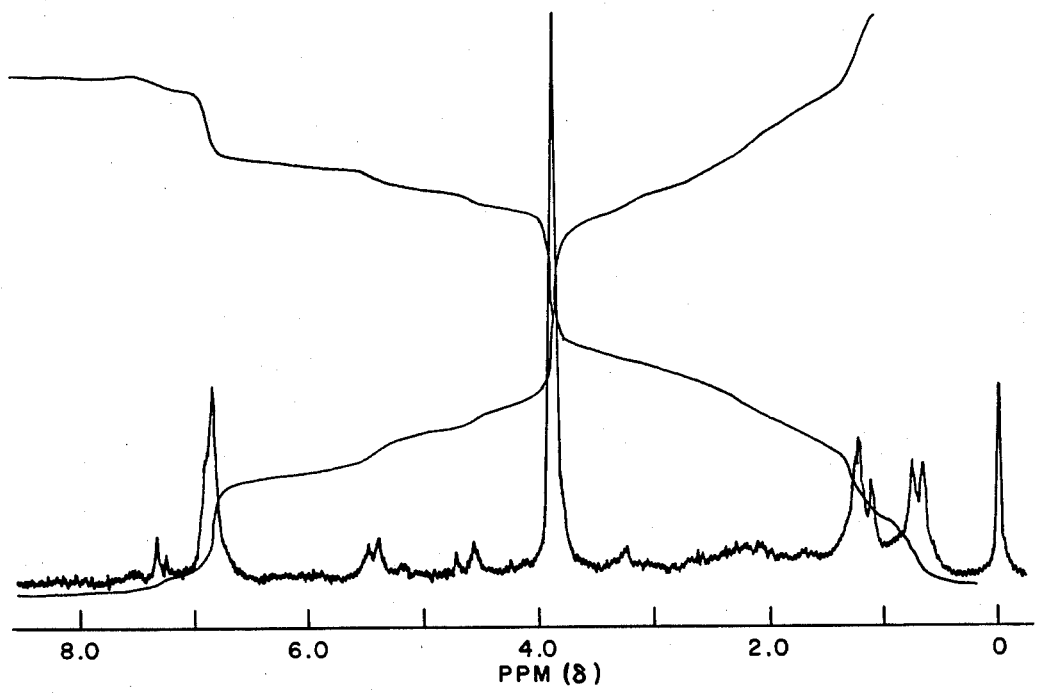

SC-5 is a colorless solid the infrared spectrum (KBr pellet) of which showed bands at 3460, 2950, 1600, 1510, 1450, 1418, 1365, 1260, 1235, 1165, 1140, 1035, 948, 925, 846, 805, and 766 cm$^{-1}$. The nmr data (CDCl$_3$, FIG. 8)

for SC-5 are as follows: τ3.17, m; τ4.52, 4.62, d; τ5.30, 5.43, d; τ5.83, m; τ6.13, s; τ7.73, m; τ8.79, 8.89, d; and τ9.23, 9.33, d. The compound had an Rf value of 0.44 on silica gel thin-layer chromatography plates when eluted with 15% acetone in benzene. The high performance liquid chromatography retention time was 3.6 minutes on a Partisil P x S 5/25 column with 1% methanol in chloroform as eluent.

Figure 4:
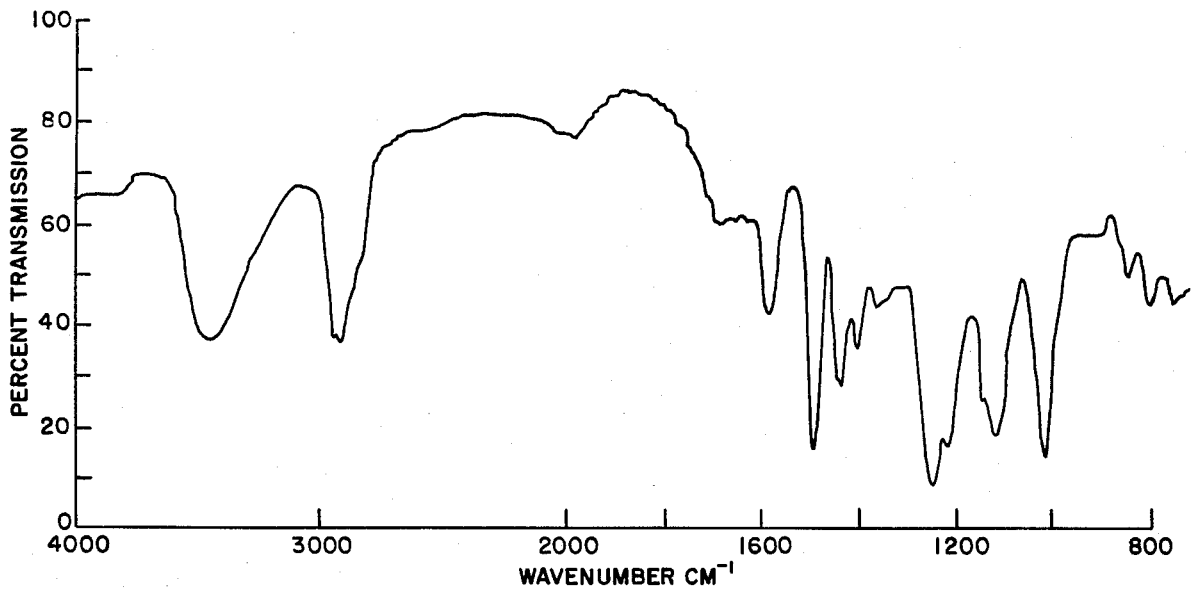
Figure 9:
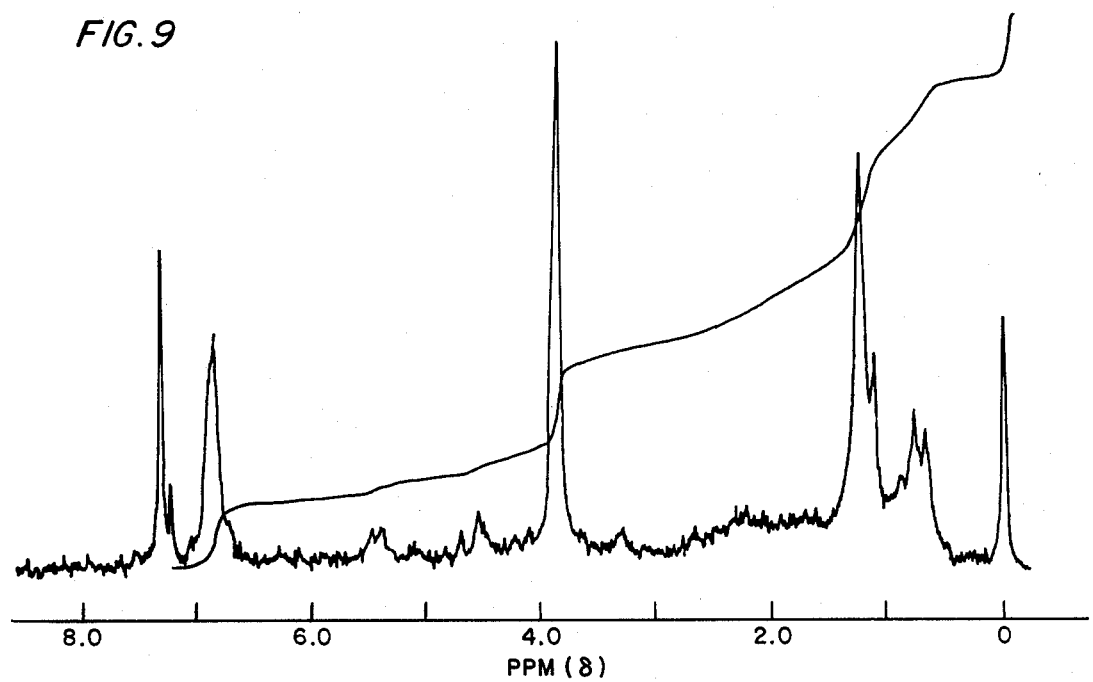

SC-9 is a colorless solid, $[\alpha]_D$-54.1 (C, 0.66 in chloroform), having infrared (KBr pellet, FIG. 4) bands at 3480, 2960, 2930, 1590, 1505, 1450, 1415, 1375, 1260, 1228, 1155, 1130, 1028, 850, 805, and 758 cm$^{-1}$. The nmr spectrum (CDCl$_3$, FIG. 9) for SC-9 showed the following signals: τ3.17, m; τ4.83, 4.93, d; τ5.30, 5.43, d; τ5.80, m; τ6.14, s; τ7.83, m; τ8.79, 8.89, d; and τ9.23, 9.33, d. SC-9 had an Rf value of 0.28 on silica gel thin-layer chromatography plates when eluted with 15% acetone in benzene.

The novel compound SC-8 has useful CNS-depressant activity as shown in experimental animals. The congeners such as SC-5, SC-7, and SC-9 which bear close structural relationship to SC-8 also show activity similar to SC-8 in mice.

SC-8 showed toxicity when injected intraperitoneally into mice. An LD$_{50}$ value was obtained according to the procedure of Turner (R. A. Turner, Screening Methods in Pharmacology, Academic Press, New York, P 302 (1965)) using ten male Swiss mice (20–25 g) per dose at doses of 10, 6.3, 4.0 and 2.5 mg/Kg. After 24 hours, the number dead at each dose was recorded and a plot of percent mortality vs log dose gave the LD$_{50}$ as 5.2±0.2 mg/Kg. SC-8 was also toxic when given by the oral route in the dose range of 10–20 mg/Kg which indicates ready absorbability following oral administration.

The behavioral assay in mice was carried out using the procedures of Campbell and Richter (D. E. S. Campbell and W. Richter, Acta Pharmacol. et Toxicol. 25, 345 (1967)). The method involved injection of five mice with the drug and obseving for sixteen behavioral signs after 30 minutes. A recognizable pattern will be apparent, characteristic of various CNS-activities: sympathomimetic, tranquilizer, etc. SC-8 showed (a) lowering of body temperature from 37° to 31°, (b) head drop with righting reflex, (c) decreased locomotion, (d) abduced hindlegs with righting reflex, (e) unsteady gait and (f) catalepsy, all of which are regarded as indicators of neuroleptic activity.

SC-8 has the ability to potentiate the sedative activity of pentobarbital. The procedure employed is that of Turner (R. A. Turner, Screening Methods in Pharmacology, Academic Press, New York, p. 302 (1965)), in which three groups of mice were injected ip with the drug at three levels and a control group with saline. Twenty minutes later, all four groups received pentobarbital (40 mg/Kg). The sleeping time of each was measured as the interval between the loss and recovery of the righting reflex, and activity is defined as at least a 200% prolongation of sleeping time.

TABLE 1

| Potentiation of Pentobarbital Sleeping Time by SC-8 | | | | |
|---|---|---|---|---|
| SC-8 mg/Kg | Pentobarbital mg/Kg | Sleeping Time Control | Treated | % Increase of Sleeping Time |
| 4.0 | 42 | 16 | 140 | 857 |
| 0.4 | 42 | 16 | 44.8 | 280 |
| 1.0 | 40 | 10.8 | 32.4 | 300 |
| 0.5 | 40 | 10.8 | 36.6 | 357 |
| 0.25 | 40 | 10.8 | 32.8 | 304 |
| 0.125 | 40 | 12.0 | 19.0 | 158 |

TABLE 1-continued

| Potentiation of Pentobarbital Sleeping Time by SC-8 | | | | |
|---|---|---|---|---|
| SC-8 mg/Kg | Pentobarbital mg/Kg | Sleeping Time Control | Treated | % Increase of Sleeping Time |
| 0.06 | 40 | 12.0 | 26.0 | 217 |
| 0.01 | 40 | 12.0 | 21.0 | 175 |

Conclusion: SC-8 showed significant prolongation of pentobarbital-sleeping time in the dose range 1.0–0.05 mg/Kg which is far below the toxic doses (LD$_{50}$: 5.2 mg/Kg, LD$_{10}$, 4 mg/Kg).

Neuroleptic drugs are said to bind to postsynaptic dopamine receptors in the brain, thereby blocking dopaminergic transmission. Certain agonists of dopamine, notably amphetamine and apomorphine exacerbate the psychoses presumably caused by dopamine. Based on this, an assay for possible neuroleptic activity was developed and is commonly used. (P. A. J. Janssen, C. G. C. Niemegeers and K. H. L. Shellekens, Arzneim Forsch. 15, 104 (1965). It involves inhibition of agitation and stereotypy in mice, rats and other experimental animals induced by dopamineagonists such as amphetamine and apomorphine. A high degree of correlation has been observed between these activities in experimental animals and the clinical potency of a neuroleptic drug (S. Fielding and H. Lal, Handbook of Psychopharmacology, L. C. Iverson, S. D. Iverson and S. H. Snyder, Eds., Plenum Press, New York P 98 (1978)). SC-8 was found to be effective in inhibiting amphetamine-induced agitation, stereotypy, and body-hydration with an ED$_{50}$ value of 0.20 mg/Kg when tested according to the method of Weissman et al. (A. Weissman, K. B. Koe and S. S. Tenen, J. Pharmacol. Exp. Therap. 151, 339 (1966)), except that mice were used instead of rats. A comparison under the same conditions was also made of the antiamphetamine activity of a standard neuroleptic drug, haloperidol, which gave an ED$_{50}$ value of 0.5 mg/Kg (Table 2).

TABLE 2

| Antiamphetamine Activity of SC-8 and Haloperidol | | | | |
|---|---|---|---|---|
| Drug | Dose mg/Kg | Log Dose | % Inhibition | ED$_{50}$ mg/Kg |
| SC-8 | 1.5 | 0.176 | 80 | |
| | 1.2 | 0.079 | 80 | |
| | 1.0 | 0 | 70 | |
| | 0.5 | −0.30 | 60 | |
| | 0.3 | −0.032 | 60 | 0.20 |
| | 0.1 | −1 | 40 | |
| | 0.03 | −1.5 | 20 | |
| Haloperidol | 1.8 | 0.25 | 90 | |
| | 1.3 | 0.11 | 70 | |
| | 1.0 | 0 | 60 | |
| | 0.75 | −0.12 | 50 | 0.50 |
| | 0.5 | −0.3 | 40 | |
| | 0.1 | −1 | 20 | |
| | 0.05 | −1.3 | 10 | |

The novel neolignans of this invention have also been found to have nematicidal properties which make them useful in agriculture or horticulture.

Nematicidal Testing Procedure

Juveniles of the nematode *Meloidogyne incognita* were placed in 10 ml vials containing 5 ml of sand each and were soaked with 3 ml of solutions of the test compound at different concentrations in 1% ethanol in water for 24 hours. Tomato seedlings (4–6″ high, with roots partly trimmed) were placed in the vials which were then placed in a growth chamber at 28° for 10 days. The tests were watered as needed to keep the sand moist. After 10 days, the plants were removed, and the galls counted on each root system. Each sample was tested in replicates of 10, and the results were analyzed according to Duncan's multiple range test (P≧0.05). The results for SC-8 are shown in Tables 3 and 4 which represent two different experiments spaced approximately two months apart. In the later test (Table 4), the amount of ethanol in the test solutions was varied.

TABLE 3

Nematicidal Activity of SC-8

| Conc[a] (ppm) | Replicate Number Number of Galls/Root System | | | | | | | | | | |
|---|---|---|---|---|---|---|---|---|---|---|---|
| | 1 | 2 | 3 | 4 | 5 | 6 | 7 | 8 | 9 | 10 | Avg. |
| 50 | 12 | 16 | 12 | 20 | 16 | 21 | 18 | 12 | 7 | 15 | 14.9[b] |
| 25 | 3 | 11 | 18 | 17 | 17 | 26 | 15 | 12 | 24 | 10 | 15.3[b] |
| 10 | 14 | 18 | 1 | 2 | 42 | 29 | 3 | 14 | 7 | 17 | 14.7[b] |
| 5 | 26 | 3 | 0 | 19 | 0 | 24 | 4 | 14 | 13 | 34 | 13.7[b] |
| 1 | 17 | 20 | 21 | 24 | 3 | 28 | 40 | 17 | 16 | 13 | 19.8[b] |
| 1% ethanol | 19 | 32 | 6 | 27 | 16 | 9 | 31 | 31 | 29 | 37 | 23.7 |
| Distilled water | 36 | 44 | 14 | 26 | 23 | 16 | 37 | 33 | 30 | 29 | 28.8 |

[a]All solutions of SC-8 contained 1% ethanol.
[b]These values are not considered significantly different from one another.

TABLE 4

Nematicidal Activity of SC-8

| Conc (ppm) | % Ethanol | Replicate Number Number of Galls/Root System | | | | | | | | | | |
|---|---|---|---|---|---|---|---|---|---|---|---|---|
| | | 1 | 2 | 3 | 4 | 5 | 6 | 7 | 8 | 9 | 10 | Avg. |
| 50 | 0.5 | 12 | 4 | 0 | 22 | 8 | 0 | 1 | 5 | 34 | 0 | 8.6[a] |
| 25 | 0.25 | 1 | 8 | 30 | 2 | 8 | 1 | 28 | 7 | 2 | 14 | 10.1[a] |
| 10 | 0.1 | 10 | 22 | 34 | 23 | 25 | 26 | 10 | 24 | 0 | 10 | 18.4[a] |
| 5 | 0.05 | 7 | 36 | 17 | 18 | 17 | 25 | 6 | 14 | 16 | 11 | 16.7[a] |
| 1 | 0.01 | 7 | 10 | 18 | 14 | 23 | 32 | 1 | 5 | 16 | 9 | 13.5[a] |
| Distilled Water | | 30 | 33 | 16 | 29 | 24 | 22 | 21 | 33 | 24 | 23 | 25.5 |

[a]These values are considered not to be significantly different from one another.

In a separate test, 300 juveniles of *M. incognita* were placed in a container closed with a screen of openings 17 μm and exposed to various concentrations of the test compound. After 24 hours, the number of nematodes able to migrate downward (from the inverted container) were counted. Eight replicates were run for each sample, and the results were analyzed by Duncan's

TABLE 5

Effect of SC-8 on Nematode Motility

| Conc (ppm) | Replicate Number Number of Motile Nematodes | | | | | | | | |
|---|---|---|---|---|---|---|---|---|---|
| | 1 | 2 | 3 | 4 | 5 | 6 | 7 | 8 | Avg. |
| 50 | 163 | 223 | 109 | 102 | 31 | 232 | 225 | 108 | 149.1[a] |
| 25 | 67 | 85 | 97 | 56 | 99 | 120 | 131 | 84 | 92.4 |
| 10 | 188 | 170 | 174 | 263 | 204 | 214 | 228 | 170 | 201.4[a] |
| 5 | 113 | 294 | 223 | 236 | 264 | 256 | 205 | 211 | 225.3 |
| 1 | 258 | 233 | 186 | 340 | 295 | 248 | 103 | 238 | 237.6 |
| Distilled Water | 204 | 245 | 290 | 222 | 284 | 176 | 183 | 265 | 233.6 |

[a]These values are not considered significantly different from each other.

Many compounds having insecticidal activity also show toxicity to fish. For example, rotenoids, pyrethrins, and DDT have significant toxicity to fish. For this reason, fish have been used frequently to indicate potential insecticidal activity. The present compounds were tested for acute toxicity to fish by the method described in "Methods For Acute Toxicity Tests With Fish, Macro-Invertebrates and Amphibians", EPA 660/3-75-009, Committee on Methods for Toxicity Tests With Aquatic Organisms, Environmental Protection Agency, Corvallis, OR, 1975.

The fish, commonly known as Missouri minnows or fat heads (Pimephales promelas, family, cyprinidae) were purchased from a local hatchery and equilibrated to the new surroundings for 24 hours. They were kept in deionized water, previously adjusted to pH 6.5 with phosphate buffer at 23° C. Sufficient oxygen was provided, and the fish were deprived of food during the test period.

Groups of six fish were placed in containers with different concentrations of the test compound. The percent mortality was recorded every 30 minutes. The LC 50 values (mg/L) and 95% confidence limits were determined from the percent mortality data after 2 hours of exposure from 6 separate replicates using the method of Lichfield and Wiloxon [(J. Pharmacology and Exp. Therepeutics, 96, 99–113 (1949))]. The results are shown in Tables 6 and 7 below.

TABLE 6

Acute Toxicity of SC-7 to Fish

| Conc (mg/L) | Replicate Number % Mortality | | | | | | |
|---|---|---|---|---|---|---|---|
| | 1 | 2 | 3 | 4 | 5 | 6 | Avg |
| 0.5 | 100 | 100 | 100 | 100 | 100 | 100 | 100 |
| 0.25 | 100 | 83 | 100 | 83 | 83 | 67 | 86 |
| 0.13 | 83 | 67 | 50 | 50 | 50 | 50 | 58 |
| 0.09 | 50 | 33 | 33 | 33 | 33 | 33 | 41 |
| 0.06 | 33 | 33 | 33 | 33 | 17 | 17 | 38 |
| 0.03 | 0 | 0 | 0 | 17 | 0 | 17 | 6 |
| 0 | 0 | 0 | 0 | 0 | 0 | 0 | 0 |

$LC_{50}$: 0.115 mg/L

TABLE 7

Acute Toxicity of SC-8 to Fish

| Conc (mg/L) | Replicate Number % Mortality | | | | | | |
|---|---|---|---|---|---|---|---|
| | 1 | 2 | 3 | 4 | 5 | 6 | Avg |
| 1.0 | 100 | 100 | 100 | 100 | 100 | 83 | 97 |
| 0.75 | 83 | 83 | 67 | 83 | 67 | 67 | 75 |
| 0.5 | 67 | 67 | 50 | 67 | 67 | 67 | 64 |
| 0.38 | 67 | 50 | 33 | 50 | 50 | 50 | 50 |
| 0.25 | 33 | 33 | 17 | 17 | 33 | 33 | 28 |

TABLE 7-continued

Acute Toxicity of SC-8 to Fish

| Conc (mg/L) | Replicate Number % Mortality | | | | | | |
|---|---|---|---|---|---|---|---|
| | 1 | 2 | 3 | 4 | 5 | 6 | Avg |
| 0.13 | 0 | 17 | 17 | 0 | 17 | 0 | 9 |
| 0 | 0 | 0 | 0 | 0 | 0 | 0 | 0 |

$LC_{50}$: 0.48 mg/L

The present compounds were tested for insecticidal activity against cabbage looper (*Trichoplusia ni* [Hubner]), and southern armyworm (*Spodoptera eridania*) at application rates of 1000 and 500 ppm. The tests were conducted in petri dishes containing a solid food source in which the test compounds had been incorporated. The petri dishes containing the treated food source were infested with second instar larvae of southern armyworms or cabbage loopers. Ten larvae per replicate and two replicates per test rate were used. Mortality data were taken 14 days after infestation. SC-7 was essentially inactive against both insect species at both application rates. SC-8 was inactive against the southern armyworm at both rates, but gave 100% and 90% mortality readings with cabbage looper at 1000 and 500 ppm respectively.

Similarly, in a test using mosquito larvae (*Aedes aegypti*) as the insect test species, SC-7 gave 15% mortality and SC-8 gave 93% mortality at an application rate of 100 ppm. In this test, one ml of a solution of 1000 ppm of the test compound in 10% acetone - 90% water was added to 9 ml of water in a culture tube. Ten mosquito larvae were added, and mortality readings were taken 24 hours later.

The following examples are provided to illustrate the processes involved in the invention and by no means do they limit the scope of the invention as set forth in the summary and claims sections.

EXAMPLE 1

Above-ground parts of Saururus cernuus L were collected, dried in the shade for 5-7 days and ground to a coarse mesh. The material (1 Kg) was taken in a suitable container and macerated with 95% ethanol with occasional stirring for 2 days. The extract was drained off, concentrated under reduced pressure (below 45° C.) to 1/20 of the original volume. Two such extractions were carried out and the combined concentrate was partitioned between water and chloroform (500 ml each), and the chloroform layer concentrated to obtain a brown glassy solid which showed characteristic neuroleptic activity in mice in the dose range of 50-200 mg/Kg.

EXAMPLE 2

The whole plant *Saururus cernuus* L was dried, ground and 1 Kg extracted with benzene in a continuous hot extraction apparatus for 24 hours. The extract was concentrated to 1/20 of the volume and partitioned between 4:1 methanol-water and hexane (500 ml each). The aqueous methanol layer was concentrated to a thick syrup and partitioned between benzene and 1:1 methanol-water (500 ml each). The benzene layer was concentrated to a small volume and applied to a column of silica gel (150 g) in benzene. The column was eluted with benzene with a gradient of acetone 0-30%. The fractions were monitored by uv absorption intensity at 280 nm and thin-layer chromatography and combined into groups based on their composition.

EXAMPLE 3

One liter quantities of hexane/benzene (9:1) and methanol/water (1:1) were equilibrated and the layers separated. Sephadex LH-20 (50 g) was stirred in the upper layer with the addition of the lower layer in portions. After 100 ml was added, the Sephadex became saturated and the slurry was poured into a column. A sample from the benzene partition prepared as in Example 2 (2 g) was taken up in a small amount of the Sephadex slurry and the slurry added to the column. Elution was carried out using the upper layer and then gradually with hexane containing 25%, 50% and 75% benzene. The fractions with 25% benzenehexane eluate contained SC-5 and SC-7 and were combined and concentrated to dryness. Similarly, the fractions from 50% benzene-hexane eluate containing SC-8 and SC-6 were combined with each other and concentrated to dryness. Fractions with 75% benzene-hexane layer contained some SC-6 and the bulk of SC-9. These were combined with each other and concentrated to dryness. By the method of this Example, it is possible to prepare mixtures of two SC-neolignans substantially free of the other SC-neolignans.

EXAMPLE 4

The mixture of SC-5 and 7 (1 g) from Example 3 was applied to a column of neutral alumina (30 g) in chloroform and developed with chloroform followed by a gradient of acetone in chloroform (0-25%). The first band to be eluated was SC-5 with 5% acetone/chloroform and as the solvent was increased to 15% acetone/chloroform, SC-7 was eluted. The SC-5 and SC-7 fractions were combined separately and concentrated to dryness. By the method of this Example, individual SC-neolignans may be prepared substantially free of other SC-neolignans.

EXAMPLE 5

A mixture of the active compounds SC-5, SC-6, SC-7, SC-8 and SC-9 from Example 2 was dissolved in chloroform to give a 5% solution and applied to high performance liquid chromatography column consisting of Partisil 5/25 (Whatman) as the adsorbant and eluted with chloroform containing increasing concentrations of methanol. Separation was monitored by uv at 280 nm. Individual band fractions were combined and concentrated to dryness to obtain biologically and chemically pure samples of SC-5, SC-6, SC-7, SC-8, and SC-9.

EXAMPLE 6

A mixture of SC-8 and SC-6 obtained as in Example 3 above was partitioned between benzene and a solution of sodium hydroxide in 50% aqueous methanol, and the two phases were separated. Acidification of the aqueous phase gave SC-6. Concentration of the benzene phase gave SC-8. A sample (1 g) of SC-8 so produced was purified further by dissolving in benzene (10 ml), filtering, and adding hexane to the filtrate until precipitation was complete. The colorless solid was filtered, washed with hexane and dried under vacuum for 24 hours. Elemental analysis: found: C, 68.66; H, 7.30; calculated for $C_{42}H_{52}O_{11}$: C, 68.83; H, 7.15. Optical rotation, $[\alpha]_D$ -100 (1% in chloroform); $LD_{50}$ in mice 5.2±0.2 mg/Kg.

EXAMPLE 7

Four Swiss male mice (20–25 g) were injected ip with morphine sulfate (20 mg/Kg). After 20 minutes, two of the morphine-dosed mice were injected with a solution of SC-8 (prepared by dissolving a weighed amount of the compound in a minimum of ethanol, and diluting with physiological saline) at a dosing rate of 1.5 mg/Kg. Morphine caused the mice to move around with their tails elevated (Straub tail phenomenon), and SC-8 counteracted this effect. The degree of elevation of the tail was noted at intervals, and the results tabulated. The control mice were treated with morphine only.

TABLE 8

Morphine-antagonism of SC-8

| | Degree of Tail Elevation | | |
|---|---|---|---|
| | Before* | After 20 min. | After 50 min. |
| Control | | | |
| 1 | 75° | 75° | 75° |
| 2 | 40° | 40° | 40° |
| Treated | | | |
| 1 | 40° | 10° | 10° |
| 2 | 40° | 10° | 10° |

*After treatment with morphine, but before treatment with SC-8.

EXAMPLE 8

Male Swiss mice, at least four weeks old, were isolated from each other in cages for three weeks, during which period they did not see other mice. They were not disturbed except for replacement of food. Under these conditions, about two thirds of the mice became aggressive as manifested by vicious attacks within one minute on a nonisolated male mouse placed in their cage. Such combative mice were divided into two groups. With one group held as the control, the mice in other group were injected with SC-8 at 2 or 1 mg/Kg. The mice were tested for aggressiveness before the injection and eighty minutes after the injection. If no fighting took place with a nonisolated mouse introduced into the cage, this was regarded as inhibition of aggressiveness (P. A. J. Janssen, A. H. Jageneau and C. J. E. Niemegeers; J. Pharmacol, Exp. Ther. 129, 471 (1960)). The experiment was repeated with SC-8 at 2 mg/Kg.

TABLE 9

Suppression of Aggressiveness by SC-8

| Dose (mg/Kg) | Number of Mice | % Inhibition of Aggressiveness |
|---|---|---|
| 2 | 3 | Pronounced (>75%) |
| 1 | 3 | Slight |
| 2 | 5 | Pronounced (>75%) |

EXAMPLE 9

Ten male Swiss mice (20–25 g) were divided into groups. One group was injected with physiological saline to serve as control. The other group was injected with 15 mg/Kg of benzene-partition sample (prepared as in Example 2) in suspension form (0.6 mg/ml) in physiological saline solution containing 0.5% carboxymethylcellulose. After 30 minutes, the mice were observed for sixteen behavioral signs as described by Campbell and Richter (D.E.S. Cambell and W. Richter, Acta Pharmacol. et Toxicol. 25, 345 (1967)). The treated mice showed the following positive signs: (1) lowering of body temperature from 37° to 31°, (2) head drop with righting reflex present, (3) decreased locomotion, (4) abduced hind legs with righting reflex present, (5) unsteady gait and (6) catalepsy. These are all considered as indicators of neuroleptic activity.

EXAMPLE 10

A solution of SC-8 (0.5 g) in oxydiethanol (10 ml) was boiled under reflux in the presence of 5% Pd/C (0.1 g) for 2 hours. The cooled mixture was diluted with water (30 ml) and extracted 3 times with benzene. The combined extract was washed with 0.1N sodium hydroxide twice and concentrated to an oil designated as Fraction A. The aqueous layers were acidified (pH 2) and extracted with ether. After concentration of the ether an oily residue was obtained, designated as Fraction B. A solution of Fraction B (0.5 g) in acetone (20 ml) was boiled under reflux in the presence of dimethyl sulfate (0.2 ml) and anhydrous potassium carbonate (3 g) for 6 hours. The mixture was filtered, the filtrate concentrated to dryness and the solid designated as Fraction C crystallized from methanol-ether.

Fraction A, a colorless oil, $C_{11}H_{16}O_2$, uv: 280, 232 nm; nmr: $\tau$3.30, s, 3H; $\tau$6.17, s, 6H; $\tau$7.33, 7.47, 7.60, t, 2H; $\tau$8.20, 8.33, 8.47, 8.60, q, 2H; $\tau$8.97, 9.07, 9.17, t, 3H. These data and tlc, ir and nmr spectral comparison with an authentic sample showed that Fraction A was identical with 3,4-dimethoxyphenylpropane, 5.

Fraction C, m.p. 134°–135°; $C_{22}H_{28}O_5$ (M±372); uv: 235, 3 282 nm; nmr: $\tau$3.10, 3.17, d, 6H; $\tau$5.32, 5.45, d, 2H; $\tau$6.13, s, 12H; $\tau$8.17, m, 2H; $\tau$8.90, 9.00, d, 6H. These properties agreed with the desciption given for galbelgin, 7, (A. J. Birch, B. Milligan, E. Smith and R. N. Speake, J. Chem. Soc., 4471 (1958)). The same reaction carried out using SC-6 produced the same products. The same reaction with SC-7 produced the same products in addition to 3,4-methylenedioxyphenylpropane.

EXAMPLE 11

A saturated solution of p-toluenesulfonic acid in benzene (25 ml) was added to SC-8 (0.5 g) and the solution boiled under reflux for 2 hours. After cooling, the mixture was washed twice with water and twice with 0.1N aqueous sodium hydroxide. The benzene layer was concentrated to an oil which was designated as Fraction A. The aqueous basic layer was acidified, extracted with ether and the extract concentrated to dryness. The semi-solid was dissolved in acetone (20 ml) and reacted with dimethyl sulfate (0.3 ml) and anhydrous potassium carbonate (3 g) for 6 hours at 60°. The mixture was filtered and the filtrate concentrated to dryness. The solid was crystallized from ether to give Fraction B, m.p. 101°, $C_{22}H_{26}O_4$. It was heated with 5% Pd/C in oxydiethanol at reflux for 1 hour. After cooling, dilution with water, extraction with ether and concentration of the ether, a crystalline solid was obtained designated as Fraction C.

Fraction A, an oil, $C_{11}H_{14}O_3$, uv: 280, ir: 1705 cm$^{-1}$; nmr: $\tau$3.25, m, 3H; $\tau$6.17, s, 6H; $\tau$6.40, s, 2H; $\tau$7.87, s, 3H was found to be identical with an authentic sample of 3,4-dimethoxyphenylacetone, 8.

Fraction B, uv: 282, 312 nm; nmr: $\tau$3.43, m, 5H; $\tau$3.97, s, 1H; $\tau$6.27, s, 13H; $\tau$8.25, s, 3H; $\tau$8.90, 9.00, d, 3H. Fraction C, m.p. 248–49°, $C_{22}H_{24}O_4$, uv: 282, 314, 329 nm, nmr: $\tau$1.95, s, 1H; $\tau$2.50, s, 1H; $\tau$3.04, m, 4H; $\tau$6.07, s, 3H; $\tau$6.17, s, 3H; $\tau$6.33, s, 6H; $\tau$7.53, s, 3H; $\tau$7.90, s, 3H. Fractions B and C were assigned the structures 9a and 10 respectively.

A number of synthetic or semi-synthetic analogs of the present SC-neolignins are exemplified in the following examples. These analogs are useful as neuroleptic agents, insecticides, or nematicides, or are useful intermediates for neuroleptic agents, insecticides, or nematicides. Any alkyl group is preferably a lower alkyl group, for example, of 1 to 4 carbon atoms.

thro and thre/erytho isomers were separated using high performance liquid chromatography. Using this procedure with the appropriate phenolic tetrahydrofuranoid neolignans, a series of biologically active analogues of SC-8 may be prepared as shown in the table.

Stereochemistry of the SC-8 Analogues

| 1 | 2 | 3 | 4 | 5 | 6 |
|---|---|---|---|---|---|
| α | α | β | β | threo | threo |
| α | α | β | β | erythro | erythro |
| α | β | α | β | threo | threo |
| α | β | α | β | erythro | erythro |
| α | β | β | α | threo | threo |
| α | β | β | α | erythro | erythro |
| β | β | β | β | threo | threo |
| β | β | β | β | erythro | erythro |
| α | β | α | α | threo | threo |
| α | β | α | α | erythro | erythro |

EXAMPLE 12

A mixture of SC-6 (0.54 g), 2'-bromo-3,4-dimethoxypropiophenone (0.3 g), and anhydrous potassium carbonate (1 g) in dimethylformamide (10 ml) was stirred at 25° for 6 hours. The mixture was diluted with water, and a solid, structure 16 above, was collected by filtration. The solid was reacted with sodium borohydride (0.1 g) in methanol (5 ml). After 10 minutes, the mixture was diluted with water (20 ml) and a solid, structure 17 above, was collected by filtration. The solid was a mixture of two isomers, threo/erythro and threo/threo, in a ratio of 4:1. The isomers were separated by high performance liquid chromatography using a column of Partisil P x S 5/25 with 1% methanol/chloroform as an eluent. In the same manner, biologically active threo/threo and threo/erythro isomers may be prepared using the following 2'-bromopropiophenones: 4-methoxy; 3,4-methylenedioxy; 3,4,5-trimethoxy; 3-methoxy-4,5-methylenedioxy; 2,5-dimethoxy-4-methyl; 2,5-dimethoxy-4-chloro; 2,5-dimethoxy-4-trifluoromethyl; 2,5-dimethoxy-4-methylthio.

EXAMPLE 13

A mixture of SC-8 (0.5 g) in 2N aqueous sodium hydroxide in 1:1 ethanol/water (25 ml) was heated in a sealed tube at 170°-180° for 2 hours. After cooling and diluting with water, the reaction mixture was extracted with benzene to remove the neutral fractions. The aqueous layer was acidified and extracted with benzene to give, after concentration of the extract, a colorless glassy solid, $C_{20}H_{24}O_5$, designated as Fraction A. Methylation of a sample of Fraction A with dimethyl sulfate gave SC-2, m.p. 80°-81°, 21.

A sample of Fraction A (0.4 g) in dimethylformamide (10 ml) was alkylated with 2'bromo-3,4-dimethoxypropiophenone (0.5 g) and potassium carbonate (2 g) in the manner described in Example 12. The reaction product was recovered and subjected to catalytic hydrogenation in the presence of Pt catalyst in a Parr apparatus. The mixture of the threo/threo, erthro/ery-

EXAMPLE 14

SC-8 (0.54 g) was reacted with acetic anhydride (5 ml) and pyridine (0.5 ml) at 50° for 1 hour. The cooled mixture was diluted with water and the solid filtered to give the biologically active diacetate derivative. In a similar manner were also prepared the following biologically active diesters: propionate, butyrate, pivalate, laurate, palmitate, dimethylaminoacetate, $N^1$-methyl-$N^2$piperazinoacetate, N-morpholinoacetate, benzoate, p-fluorobenzoate, hemi-succinate, and hemi-maleate. The same derivatives of SC-7 may be prepared in a similar manner.

EXAMPLE 15

A solution of SC-8 (0.5 g) in dioxane (25 ml) was hydrogenated in the presence of 5% Pd/C in a Parr apparatus at 50 p.s.i. for 24 hours. The reaction mixture was freed from the catalyst and concentrated to dryness to yield the biologically active dideoxy derivative. The dideoxy derivative of SC-7 may also be prepared in this manner.

EXAMPLE 16

SC-8 (0.5 g) dissolved in dimethylformamide (10 ml) was stirred with sodium hydride (0.3 g) and, 30 minutes later, methyl iodide (0.5 g) was added and the mixture stirred for 20 hours. It was diluted with water, extracted with ether and the extract purified by chromatography on silica gel to recover the pure biologically active dimethyl ether. In a similar manner, by using benzyl chloride, p-fluorobenzylchloride, allyl bromide, and bromoacetone, the corresponding biologically active diethers of SC-8 were prepared. The same derivatives of SC-7 may also be prepared by this method.

EXAMPLE 17

A solution of SC-7 in acetone was cooled to 5° C. and titrated with 1M chromic acid in 1N sulfuric acid until the starting material reacted completely as indicated by thin-layer chromatography. After five minutes, the mixture was diluted with water, extracted with benzene and the extract concentrated to dryness to yield the biologically active didehydro derivative. By using the same procedure the didehydro derivatives of SC-5, SC-8, and SC-9 were prepared.

EXAMPLE 18

A mixture of 2'-bromo-3,4-dimethoxypropiophenone (1.5 mM), anhydrous potassium carbonate (2 mM) and vanillin (1 mM) in dimethyl formamide was stirred for six hours at 25° C. It was diluted with water, the solid filtered and crystallized from ether-hexane. By using this same general procedure, a variety of phenolic and amino compounds may be alkylated to yield compounds of the basic structure:

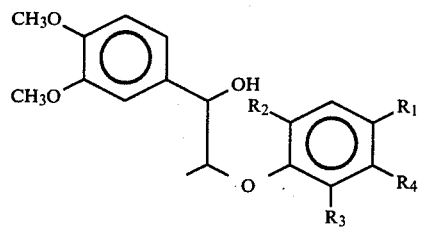

threo/erythro

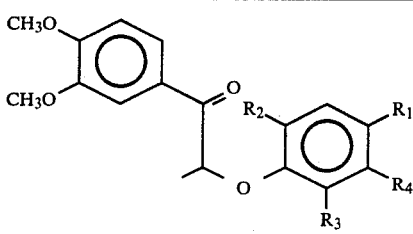

| Compound alkylated | Product | | | |
|---|---|---|---|---|
| | $R_1$ | $R_2$ | $R_3$ | $R_4$ |
| Vanillin | CHO | H | $OCH_3$ | H |
| Isovanillin | H | $OCH_3$ | H | CHO |
| Isovanillic acid | H | $OCH_3$ | H | COOH |
| Isovanillic acid lower alkyl ester | H | $OCH_3$ | H | COO—Alk |
| Isovanillyl alcohol | H | $OCH_3$ | H | $CH_2OH$ |
| Acetovanillone | $COCH_3$ | H | $OCH_3$ | H |
| Propiovanillone | $COCH_2CH_3$ | H | $OCH_3$ | H |
| Vanillic acid | COOH | H | $OCH_3$ | H |
| Vanillic acid lower alkyl ester | COO—Alk | H | $OCH_3$ | H |
| Vanillyl alcohol | $CH_2OH$ | H | $OCH_3$ | H |
| Vanillidine acetone | $CH=CH-COCH_3$ | H | $OCH_3$ | H |
| Eugenol | $CH_2-CH=CH_2$ | H | $OCH_3$ | H |
| Epoxyeugenol | $CH_2-CH\underset{O}{\overset{}{-\!-\!-}}CH_2$ | H | $OCH_3$ | H |
| Isoeugenol | $CH=CH-CH_3$ | H | $OCH_3$ | H |
| Epoxyisoeugenol | $CH\underset{O}{\overset{}{-\!-\!-}}CH-CH_3$ | H | $OCH_3$ | H |
| Vanillylamine | $CH_2NH_2$ | H | $OCH_3$ | H |
| Homovanillylamine | $CH_2CH_2NH_2$ | H | $OCH_3$ | H |
| Vanillylisopropylamine | $CH_2CH-CH_3$ $NH_2$ | H | $OCH_3$ | H |
| Vanillylpropylamine, N,N—dialkyl | $CH_2CH_2CH_2NAlk_2$ | H | $OCH_3$ | H |

EXAMPLE 19

The compounds described in Example 18 may be subjected to catalytic hydrogenation to yield the corresponding hydroxy compounds (threo and erythro isomers). The isomers may be separated by high performance liquid chromatography. The nature of the substituents in the product shown below is the same as the shown in Example 18.

EXAMPLE 20

The following compounds may be prepared by the alkylation process described in Example 12. In the starting material, R=H. In the product,

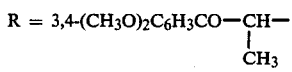

R = 3,4-$(CH_3O)_2C_6H_3CO-CH-$
                                     |
                                     $CH_3$

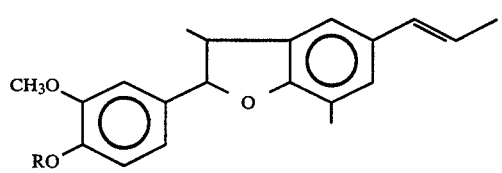

-continued
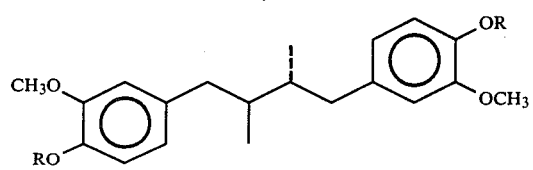
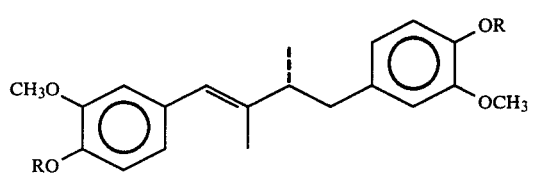
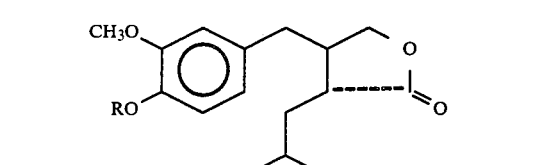
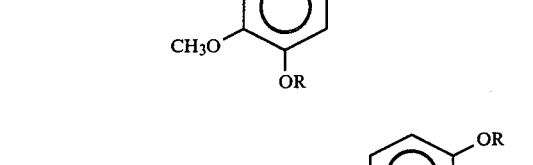
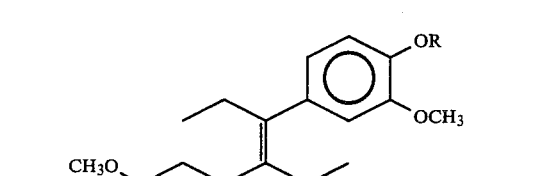
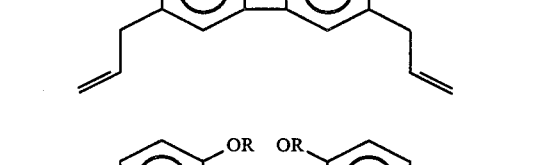
-continued
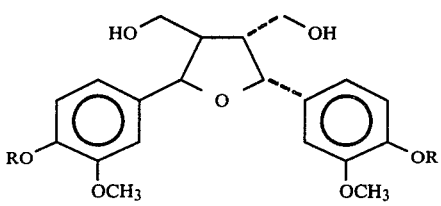
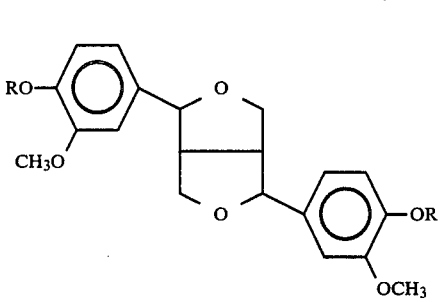
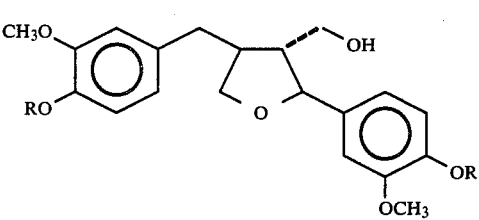
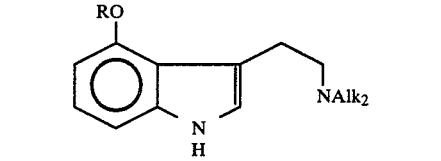
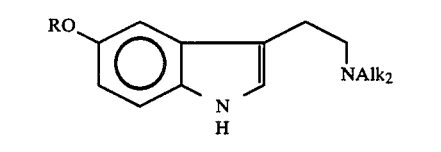
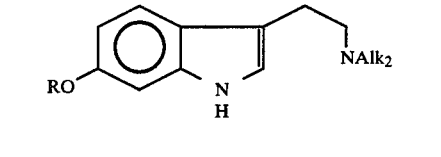
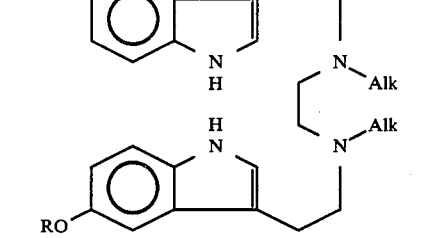
EXAMPLE 21
The compounds described in Example 20 may be subjected to catalytic hydrogenation to give the corresponding hydroxy compounds (threo and erythro isomers). The isomers may be separated by high performance liquid chromatography as described under Example 13. For each compound listed under Example 20, the product here has

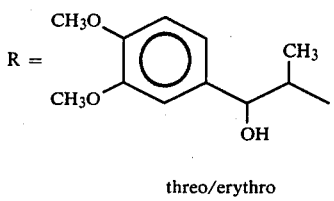

threo/erythro

I claim:
1. The SC-neolignan
   (A) SC-5 having an Rf value of 0.44 on silica gel thin-layer chromatography plates when eluted with 15% acetone in benzene; a high performance liquid chromatography retention time of 3.6 minutes on a Partisil P x S 5/25 column when eluted with 1% methanol in chloroform; infrared bands when pelleted with KBr at 3460, 2950, 1600, 1510, 1450, 1418, 1365, 1260, 1235, 1165, 1140, 1035, 948, 925, 846, 805, and 766 cm$^{-1}$; and, in solution in CDCl$_3$, nmr peaks ($\tau$values) as follows: 3.17 (m), 4.52 and 4.62 (d), 5.30 and 5.43 (d), 5.83 (m), 6.13 (s), 7.73 (m), 8.79 and 8.89 (d), and 9.23 and 9.33 (d);

(B) SC-9 having an optical rotation of $[\alpha]_D = -54.1$ at a concentration of 0.66% in CHCl$_3$; an Rf value of 0.28 on silica gel thin-layer chromatography plates when eluted with 15% acetone in benzene; infrared bands when pelleted with KBr at 3480, 2960, 2930, 1590, 1505, 1450, 1415, 1375, 1260, 1228, 1155, 1130, 1028, 850, 805, and 758 cm$^{-1}$; and, in solution in CDCl$_3$, nmr peaks ($\tau$values) as follows: 3.17 (m), 4.83 and 4.93 (d), 5.30 and 5.43 (d), 5.80 (m), 6.14 (s), 7.83 (m), 8.79 and 8.89 (d), and 9.23 and 9.33 (d);

(C) SC-6, 2α-(4-hydroxy-3-methoxy)phenyl-5β-[3-methoxy-4-{threo-3-hydroxy-3-(3,4-dimethoxyphenyl)}isopropoxyphenyl]-3α,4β-dimethyltetrahydrofuran;

(D) SC-7, 2α-[3-methoxy-4-{threo-3-hydroxy-3-(-3,4-dimethoxyphenyl)}isopropoxyphenyl]-5β-[3-methoxy-4-{threo-3-hydroxy-3-(3,4-methylenedioxyphenyl}isopropoxyphenyl]-3α,4β8-dimethyltetrahydrofuran; or (E) SC-8, 2α,5β-bis[3-methoxy-4-{threo-3-hydroxy-3-(3,4-dimethoxyphenyl)}isopropoxyphenyl]-3α,4β-dimethyltetrahydrofuran.

2. The SC-neolignan of claim 1 designated SC-5.
3. The SC-neolignan of claim 1 designated SC-6.
4. The SC-neolignan of claim 1 designated SC-7.
5. The SC-neolignan of claim 1 designated SC-8.
6. The SC-neolignan of claim 1 designated SC-9.
7. A SC-neolignan of claim 1 substantially free of watersoluble plant material.
8. A SC-neolignan of claim 1 substantially free of other SC-neolignans.
9. A mixture of two or more SC-neolignans of claim 1 substantially free of water-soluble plant material.
10. A mixture of two SC-neolignans of claim 1, substantially free of other SC-neolignans, selected from the group of mixtures consisting of (i) SC-5 and SC-7, (ii) SC-6 and SC-8, and (iii) SC-6 and SC-9.
11. A compound of the formula

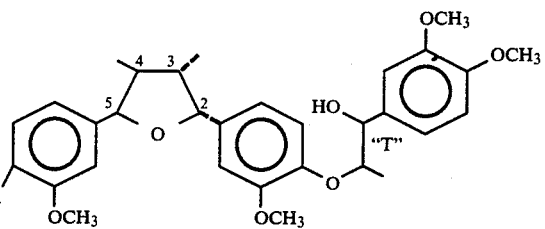

in which bonds 2 and 3 are α and 4 and 5 are β, "T" is threo, and R is hydroxy, threo or erythro 3-hydroxy-3-(3,4-dimethoxyphenyl)isopropoxy, or threo or erythryo 3-hydroxy-3-(3,4-methylenedioxyphenyl)isopropoxy.

12. A compound of the formula

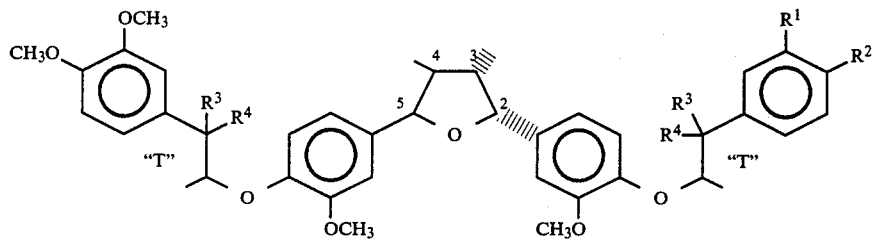

in which bonds 2 and 3 are α and 4 and 5 are β, each of R$^1$ and R$^2$ is a methoxy group or R$^1$ and R$^2$ taken together form a methylenedioxy group, and R$^3$ and R$^4$ are selected as follows:
   (A) each of R$^3$ and R$^4$ is hydrogen;
   (B) R$^3$ and R$^4$ together from a divalent oxygen atom O=; or
   (C) one of R$^3$ and R$^4$ is hydrogen and the other is —OR$^5$ in which R$^5$ is a hydrogen atom or a radical selected from the group consisting of methyl, benzyl, p-fluorobenzyl, allyl, 2-oxopropyl, acetyl, propionyl, butyryl, pivalyl, lauryl, palmityl, dimethylaminoacetyl, N$^1$-methyl-N$^2$-piperazinoacetyl, morpholinoacetyl, benzoyl, p-fluorobenzoyl, carboxymethylacetyl, and carboxymethinylacetyl, and "T" is threo.

13. A compound of claim 12 in which each of R$^1$ and R$^2$ is a methoxy group.

14. The compound of claim 13 in which each of R$^3$ and R$^4$ is hydrogen.

15. The compound of claim 13 in which R$^3$ and R$^4$ together form a divalent oxygen atom.

16. The compound of claim 13 in which one of R$^3$ and R$^4$ is hydrogen and the other is —OR$^5$ in which R$^5$ is a radical selected from the group consisting of methyl, benzyl, p-fluorobenzyl, allyl, and 2-oxopropyl.

17. The compound of claim 13 in which one of R$^3$ and R$^4$ is hydrogen and the other is —OR$^5$ in which R$^5$ is a radical selected from the group consisting of acetyl, propionyl, butyryl, pivalyl, lauryl, palmityl, dimethylaminoacetyl, $N^1$-methyl-$N^2$-piperazinylacetyl, morpholinoacetyl, benzoyl, p-fluorobenzoyl, carboxymethylacetyl, and carboxymethinylacetyl.

18. A compound of the formula

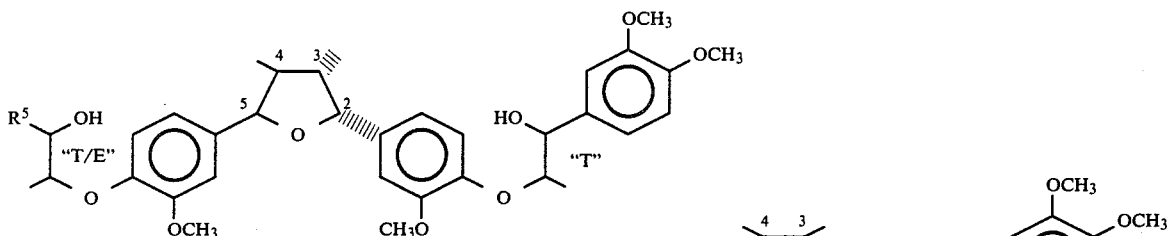

in which bonds 2 and 3 are α and 4 and 5 are β, "T" is threo, "T/E" is threo or erythro, and $R^5$ is a substituted-phenyl radical selected from the group consisting of 4-methoxyphenyl, 3,4-dimethoxyphenyl, 3-4-methylenedioxyphenyl, 3,4,5-trimethoxyphenyl, 3-methoxy-4,5-methylenedioxyphenyl, 2,5-dimethoxy-4-methylphenyl, 2,5-dimethoxy-4-chlorophenyl, 2,5-dimethoxy-4-trifluoromethylphenyl, and 2,5-dimethoxy-4-methylthiophenyl.

19. A compound of the formula

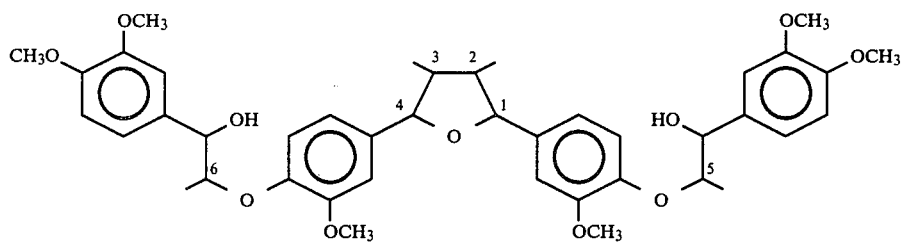

wherein 1, 2, 3, 4, 5, and 6 are selected from the group consisting of

| 1 | 2 | 3 | 4 | 5 | 6 |
|---|---|---|---|---|---|
| α | α | β | β | threo | threo |
| α | α | β | β | erythro | erythro |
| α | β | α | β | threo | threo |
| α | β | α | β | erythro | erythro |
| α | β | β | α | threo | threo |
| α | β | β | α | erythro | erythro |
| β | β | β | β | threo | threo |
| β | β | β | β | erythro | β erythro |
| α | β | α | α | threo | threo |
| α | β | α | α | erythro | erythro |

20. A compound of the formula in which bonds 2 and 3, 3 and 4, and 4 and 5 are cis/trans/cis respectively without regard to absolute configuration, "T" is threo, and R is hydroxy, threo or erythro 3-hydroxy-3-(3,4-dimethoxyphenyl)isopropoxy, or threo or erythro 3-hydroxy-3-(3,4-methylenedioxyphenyl)isopropoxy.

21. A compound of the formula

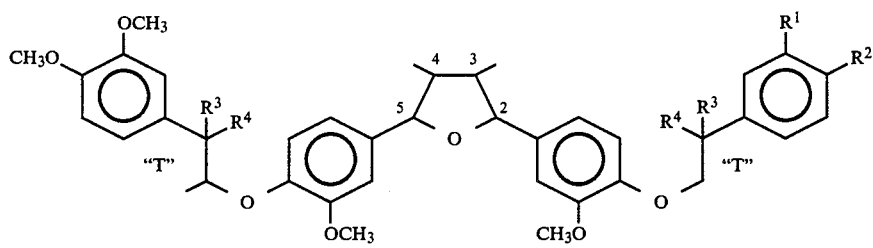

in which bonds 2 and 3, 3 and 4, and 4 and 5 are cis/trans/cis respectively without regard to absolute configuration, each of $R^1$ and $R^2$ is a methoxy group or $R^1$ and $R^2$ taken together form a methylenedioxy group, and $R^3$ and $R^4$ are selected as follows:

(A) each of $R^3$ and $R^4$ is hydrogen;
(B) $R^3$ and $R^4$ together from a divalent oxygen atom O=; or
(C) one of $R^3$ and $R^4$ is hydrogen and the other is —$OR^5$ in which $R^5$ is a hydrogen atom or a radical selected from the group consisting of methyl, benzyl, p-fluorobenzyl, allyl, 2-oxopropyl, acetyl, propionyl, butyryl, pivalyl, lauryl, palmityl, dimethylaminoacetyl, $N^1$-methyl-$N^2$-piperazinoacetyl, morpholinoacetyl, benzoyl, p-fluorobenzoyl, carboxymethylacetyl, and carboxymethinylacetyl, and "T" is threo.

22. A compound of the formula

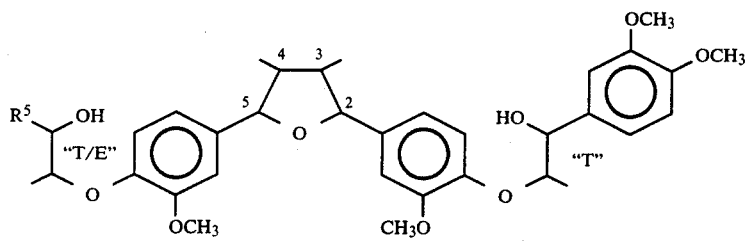

in which bonds 2 and 3, 3 and 4, and 4 and 5 are cis/trans/cis respectively without regard to absolute configuration, "T" is threo, "T/E" is threo or erythro, and $R^5$ is a substituted-phenyl radical selected from the group consisting of 4-methoxyphenyl, 3,4-dimethoxyphenyl, 3-4-methylenedioxyphenyl, 3,4,5-trimethoxyphenyl, 3-methoxy-4,5-methylenedioxyphenyl, 2,5-dimethoxy-4-methylphenyl, 2,5-dimethoxy-4-chlorophenyl, 2,5-dimethoxy-4-trifluoromethylphenyl, and 2,5-dimethoxy-4-methylthiophenyl.

23. A neuroleptic composition comprising a neuroleptically effective amount of the compound SC-5, SC-7, SC-8, or SC-9 of claim 1 in admixture with a pharmaceutically acceptable carrier.

24. The neuroleptic composition of claim 23 in which the compound is SC-8.

25. A neuroleptic composition comprising a neuroleptically effective amount of the compound of claim 20 in admixture with a pharmaceutically acceptable carrier.

26. A method of inducing a neuroleptic response in a warm-blooded animal, which comprises administering to such animal a neuroleptically effective amount of the neuroleptic composition of claim 23.

* * * * *